US012127977B2

(12) United States Patent
Goetz

(10) Patent No.: US 12,127,977 B2
(45) Date of Patent: *Oct. 29, 2024

(54) ULTRASONIC OPHTHALMIC DEVICE

(71) Applicant: Verily Life Sciences LLC, Dallas, TX (US)

(72) Inventor: Georges Goetz, Mountain View, CA (US)

(73) Assignee: Verily Life Sciences LLC, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/240,978

(22) Filed: Aug. 31, 2023

(65) Prior Publication Data

US 2023/0404800 A1    Dec. 21, 2023

Related U.S. Application Data

(63) Continuation of application No. 16/352,215, filed on Mar. 13, 2019, now Pat. No. 11,744,731.

(Continued)

(51) Int. Cl.
*A61F 9/00*    (2006.01)
*A61B 8/00*    (2006.01)
(Continued)

(52) U.S. Cl.
CPC ............ *A61F 9/0017* (2013.01); *A61B 8/085* (2013.01); *A61B 8/10* (2013.01); *A61B 8/54* (2013.01);
(Continued)

(58) Field of Classification Search
CPC ...... A61F 9/0017; A61F 2/1624; A61F 2/482; A61F 2250/0001; A61F 2250/0002;
(Continued)

(56) References Cited

U.S. PATENT DOCUMENTS 8,043,370 B2    10/2011    Bretthauer et al.
8,409,278 B2    4/2013    Peyman et al.
(Continued)

FOREIGN PATENT DOCUMENTS

CA    2 678 025 A1    8/2008
JP    2017-113136 A    6/2017
(Continued)

OTHER PUBLICATIONS

Anatomy of Ciliary Body, Ciliary Processes, Anterior Chamber Angle and Collector Vessels, IntechOpen, Retrieved ram Internet: <https://www.intechopen.com/books/glaucoma-basic-and-clinical-aspects/anatomy-of-ciliary-body-ciliaryt>rocesses-anterior-chamber-angle-and-collec%E2%80%A6> Feb. 27, 2019, 19 pages.

(Continued)

*Primary Examiner* — Peter Luong
(74) *Attorney, Agent, or Firm* — Christensen O'Connor Johnson Kindness PLLC

(57) ABSTRACT

An ophthalmic device comprises an ultrasonic transducer, an accommodation actuator, and a controller. When the ophthalmic device is mounted in or on an eye of a user, the ultrasonic transducer is positioned to direct ultrasonic signals towards ciliary processes in the eye and the accommodation actuator is positioned to focus light entering the eye. The controller is coupled to the ultrasonic transducer and the accommodation actuator. The controller includes logic that when executed by the controller causes the ophthalmic device to perform operations including emitting the ultrasonic signals from the ultrasonic transducer towards the ciliary processes, receiving reflected ultrasonic signals from the ciliary processes with the ultrasonic transducer, calculating a time of flight between emitting the ultrasonic signals and receiving the reflected ultrasonic signals, and adjusting (Continued)

an optical power of the accommodation actuator based on the time of flight.

20 Claims, 10 Drawing Sheets

Related U.S. Application Data

(60) Provisional application No. 62/643,509, filed on Mar. 15, 2018.

(51) Int. Cl.
*A61B 8/08* (2006.01)
*A61B 8/10* (2006.01)
*A61F 2/16* (2006.01)
*A61F 2/48* (2006.01)
*G02C 7/04* (2006.01)

(52) U.S. Cl.
CPC .... *A61F 2/1624* (2013.01); *A61B 2562/0204* (2013.01); *A61B 2562/0257* (2013.01); *A61F 2/482* (2021.08); *A61F 2250/0001* (2013.01); *A61F 2250/0002* (2013.01); *G02C 7/04* (2013.01)

(58) Field of Classification Search
CPC .. A61B 8/085; A61B 8/10; A61B 8/54; A61B 2562/0204; A61B 2562/0257
See application file for complete search history.

(56) References Cited

U.S. PATENT DOCUMENTS

| | | | |
|---|---|---|---|
| 8,834,566 | B1 | 9/2014 | Jones |
| 9,226,818 | B2 | 1/2016 | Campin et al. |
| 10,495,902 | B2* | 12/2019 | Pugh .................. G02C 7/049 |
| 2012/0323228 | A1 | 12/2012 | Peyman |
| 2015/0087991 | A1 | 3/2015 | Chen et al. |
| 2015/0173600 | A1 | 6/2015 | Campin et al. |
| 2015/0173893 | A1 | 6/2015 | Portney |
| 2015/0362756 | A1 | 12/2015 | Wiser et al. |
| 2016/0038119 | A1 | 2/2016 | Desjardins |
| 2017/0079771 | A1 | 3/2017 | Roholt et al. |
| 2019/0105519 | A1 | 4/2019 | Herekar et al. |
| 2020/0257136 | A1 | 8/2020 | Arbabian et al. |

FOREIGN PATENT DOCUMENTS

| | | |
|---|---|---|
| WO | 2012006691 A1 | 1/2012 |
| WO | 2017191542 A1 | 11/2017 |
| WO | 2017212354 A1 | 12/2017 |

OTHER PUBLICATIONS

Capacitive Micromachined Ultrasonic Transducers, Phillips Innovation Services, Retrieved from Internet: <https:1/WWW.innovationservices.philips.com/looking-for-expertise/> Feb. 27, 2019, 8 pages.
Khuri-Yakub, B.T. et al., "Capacitive Micromachined Ultrasonic Transducers for Medical Imaging and Therapy", Uournal of Micromech Microeng. May 2011, 21 pages.
Park, K. et al., "Capacitive Micromachined Ultrasonic Transducer (CMUT) as a Chemical Sensor for DMMP Detection", Sensors and Actuators B 160, 2011, 8 pages.
Phased Array—Wikipedia page, Retrieved from Internet on Feb. 28, 2019, 13 pages.
Qiu, Y. et al., "Piezoelectric Micromachined Ultrasonic Transducers (PMUT) Arrays for Integrated Sensing, Actuation and Imaging", Sensors 2015, vol. 15, Apr. 3, 2015, 22 pages.
International Search Report and Written Opinion mailed Jul. 2, 2019, issued in corresponding International Application No. PCT/US2019/022354, filed Mar. 14, 2019, 35 pages.
Indian Office Action, mailed Jun. 30, 2021, in corresponding Indian Patent Application No. 202047041970, 5 pages.
Chinese Office Action, issued Jan. 5, 2023, in corresponding Chinese Patent Application No. 201980019363.0, 11 pages.
US Office Action issued Mar. 31, 2022, in corresponding U.S. Appl. No. 16/352,215, 5 pages.
US Office Action issued Oct. 25, 2022, in corresponding U.S. Appl. No. 16/352,215, 7 pages.
US Office Action issued Feb. 16, 2023, in corresponding U.S. Appl. No. 16/352,215, 11 pages.
US Notice of Allowance issued Apr. 26, 2023, in corresponding U.S. Appl. No. 16/352,215, 5 pages.
Chinese Notice of Allowance, issued Nov. 29, 2023, for corresponding Chinese Patent Application No. 201980019363.0, 7 pages.
Chinese Office Action issued Aug. 17, 2023, for corresponding Chinese Patent Application No. 201980019363.0, 6 pages.

* cited by examiner

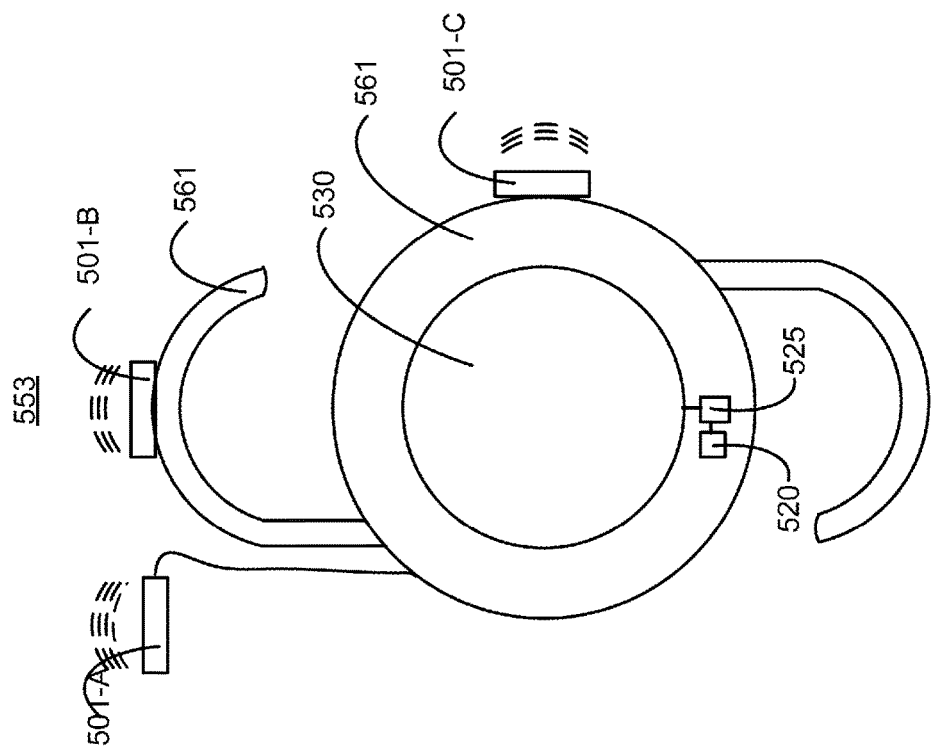
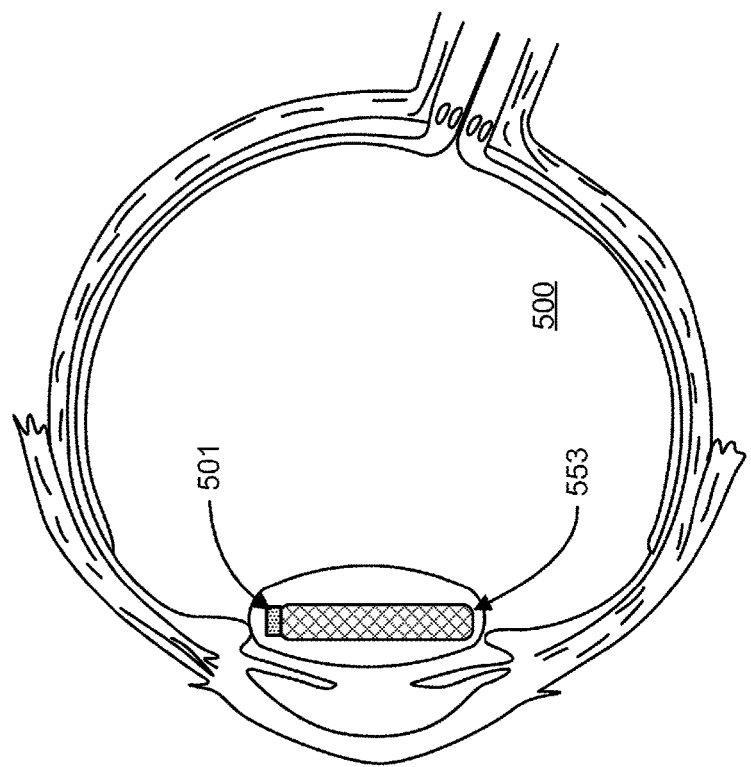
FIG. 5B
FIG. 5A

ULTRASONIC OPHTHALMIC DEVICE

CROSS-REFERENCE TO RELATED APPLICATIONS

This application is a continuation of U.S. application Ser. No. 16/352,215, filed Mar. 13, 2019, which claims the benefit of U.S. Provisional Application No. 62/643,509, filed Mar. 15, 2018, all of which contents are hereby incorporated by reference.

TECHNICAL FIELD

This disclosure relates generally to the field of optics, and in particular but not exclusively, relates to ophthalmic devices.

BACKGROUND INFORMATION

Accommodation is a process by which the eye adjusts its focal distance to maintain focus on objects of varying distance. Accommodation is a reflex action, but can be consciously manipulated. Accommodation is controlled by contractions of the ciliary muscle. The elastic lens of the eye is encircled and maintained in position by the zonular apparatus, which is manipulated, at least in part, by the ciliary muscle to change the focal point of the elastic lens.

As an individual ages, the effectiveness of the elastic lens degrades. Presbyopia is a progressive age-related loss of accommodative or focusing strength of the eye, which results in increased blur at near distances. This loss of accommodative strength with age has been well studied and is relatively consistent and predictable. Presbyopia affects nearly 1.7 billion people worldwide today (110 million in the United States alone) and that number is expected to substantially rise as the world's population ages. Techniques and devices that can help individuals offset the effects of presbyopia are increasingly in demand.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

FIGS. 5A & 5B illustrate an accommodating intraocular lens, in accordance with an embodiment of the disclosure

DETAILED DESCRIPTION

Figure 1:
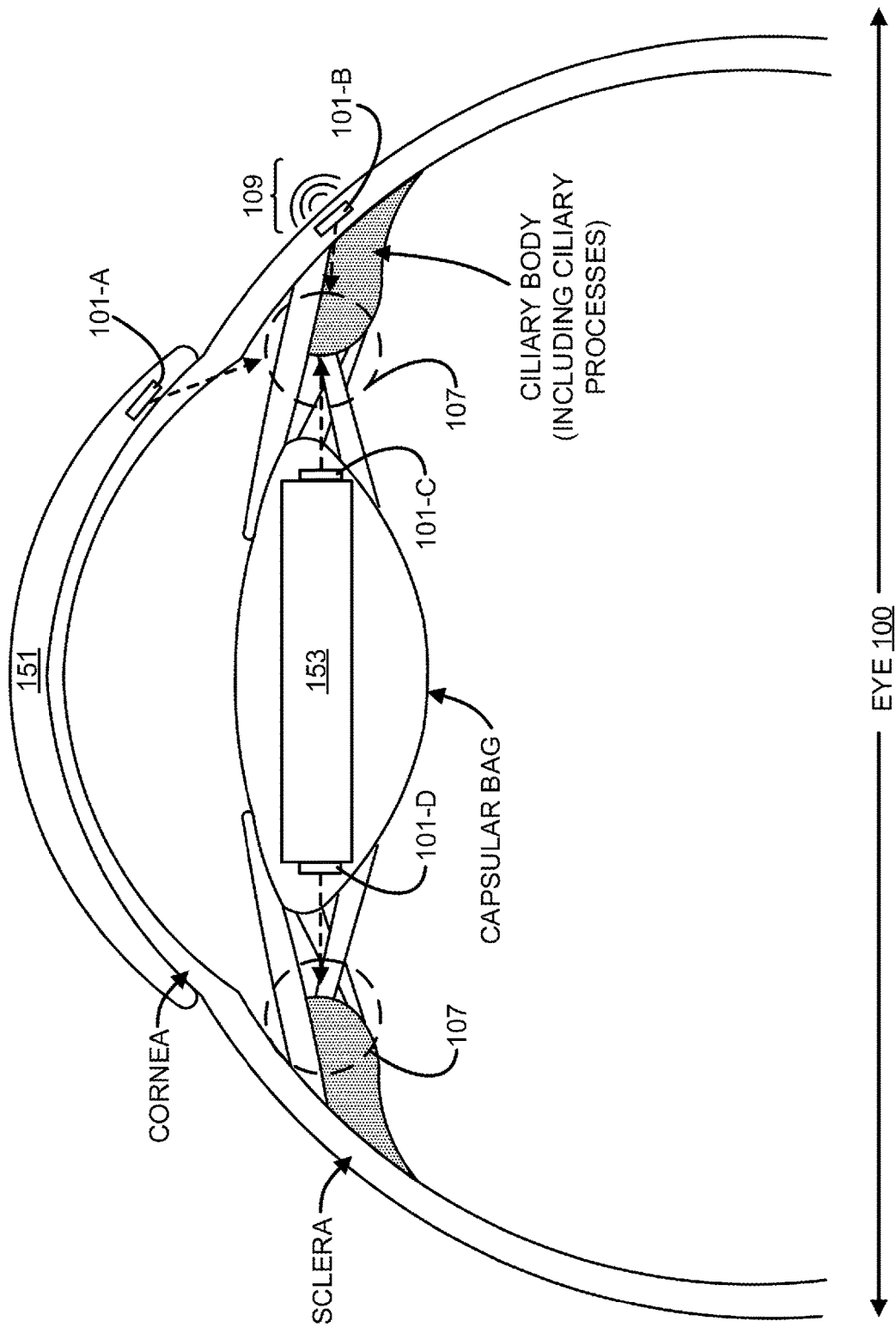
FIG. 1 illustrates exemplary placements of an ultrasonic transducer device in an eye of a user, in accordance with an embodiment of the disclosure.

Embodiments described herein variously provide an apparatus, system and/or method for an ultrasonic ophthalmic device. In the following description numerous specific details are set forth to provide a thorough understanding of the embodiments. One skilled in the relevant art will recognize, however, that the techniques described herein may be practiced without one or more of the specific details, or with other methods, components, materials, etc. In other instances, well-known structures, materials, or operations are not shown or described in detail to avoid obscuring certain aspects.

Reference throughout this specification to "one embodiment", "an embodiment", "one example" or "an example" means that a particular feature, structure, or characteristic described in connection with the embodiment is included in at least one embodiment of the present invention. Thus, the appearances of the phrases "in one embodiment", "in an embodiment", "in one example" or "in an example" in various places throughout this specification are not necessarily all referring to the same embodiment. Furthermore, the particular features, structures, or characteristics may be combined in any suitable manner in one or more embodiments.

Described herein are embodiments of ophthalmic devices, systems, and methods which utilize ultrasonic sensing of ciliary displacements (e.g., due to an accommodative effort of a user or wearer of the ophthalmic device) to control a level of accommodation provided by the ophthalmic device (e.g., for treating presbyopia). Specific embodiments provide details regarding how a transducer may be designed, how an ultrasonic wavefront (e.g., beam) emitted by the transducer may be shaped, and where the transducer may be placed.

In some embodiments, the ultrasonic transducer may rely on hard ceramic materials exhibiting piezoelectricity to perform their emission (e.g., of ultrasonic wavefronts) and/or measurements (e.g., of reflected ultrasonic wavefronts or signals). The most popular piezoceramic is PZT (lead zirconate titanium), but others, such as potassium niobate, sodium tungstate, composite variations of these materials, and otherwise may also be used. However, limitations of piezoceramic crystals may stand in the way of implementing ultrasonic sensing of ciliary displacement. For example, many of these materials contain toxic elements (e.g., lead, nickel, etc.), which may be undesirable in an implanted device, and for which encapsulation schemes to make the ophthalmic device biocompatible may be difficult to implement.

Additionally, piezoceramic transducers may operate in thickness mode, for which the thickness of the material determines the frequency at which the sensor operates. For some embodiments, size of the ophthalmic devices is an important consideration. For example, in embodiments where the ophthalmic device is an implantable device, such as an intraocular lens (e.g., in an intra-capsular configuration, where many or all the components are contained inside the capsular bag of the eye) or a scleral configuration where the ophthalmic device is a two-part intraocular lens (e.g., in which an ultrasonic transducer would be placed underneath the conjunctiva of the eye), size restrictions may exist for each component (or collectively) of the ophthalmic device, to maintain compatibility with inserting the ophthalmic device through a small incision (e.g., in the cornea or the conjunctiva).

Furthermore, it is noted that ceramic transducers may suffer from poor yield when manufactured to perform at frequencies desired for ophthalmic applications while also considering size limitations. For example, the grain of piezoelectric crystals may be comparable to the target thickness of the transducer for ophthalmic applications, which may result in imperfections degrading performance of the transducer.

Accordingly, embodiments of ophthalmic devices disclosed herein may circumvent limitations associated with piezoelectric ceramic crystals. One of skill in the art will appreciate, however, that despite the limitations discussed above, some piezoelectric materials may still be compatible with, and useful for, the embodiments of ophthalmic devices disclosed herein.

In some embodiments, ophthalmic devices utilizing one or more micromachined ultrasonic transducers (MUTs) may be leveraged to provide an implanted device that may survive for twenty or more years in the body after being injected through a very small incision. MUTs offer several advantages over piezoelectric ceramic transducers that address issues with (1) the operating frequency of the transducer, (2) the packaging requirements of the transducer, and (3) integration of the fabrication process for the transducer with standard CMOS processes (e.g., to compliment fabrication of the transducer with the fabrication or design of the custom integrated circuits driving the ophthalmic devices disclosed herein).

Figure 2A:
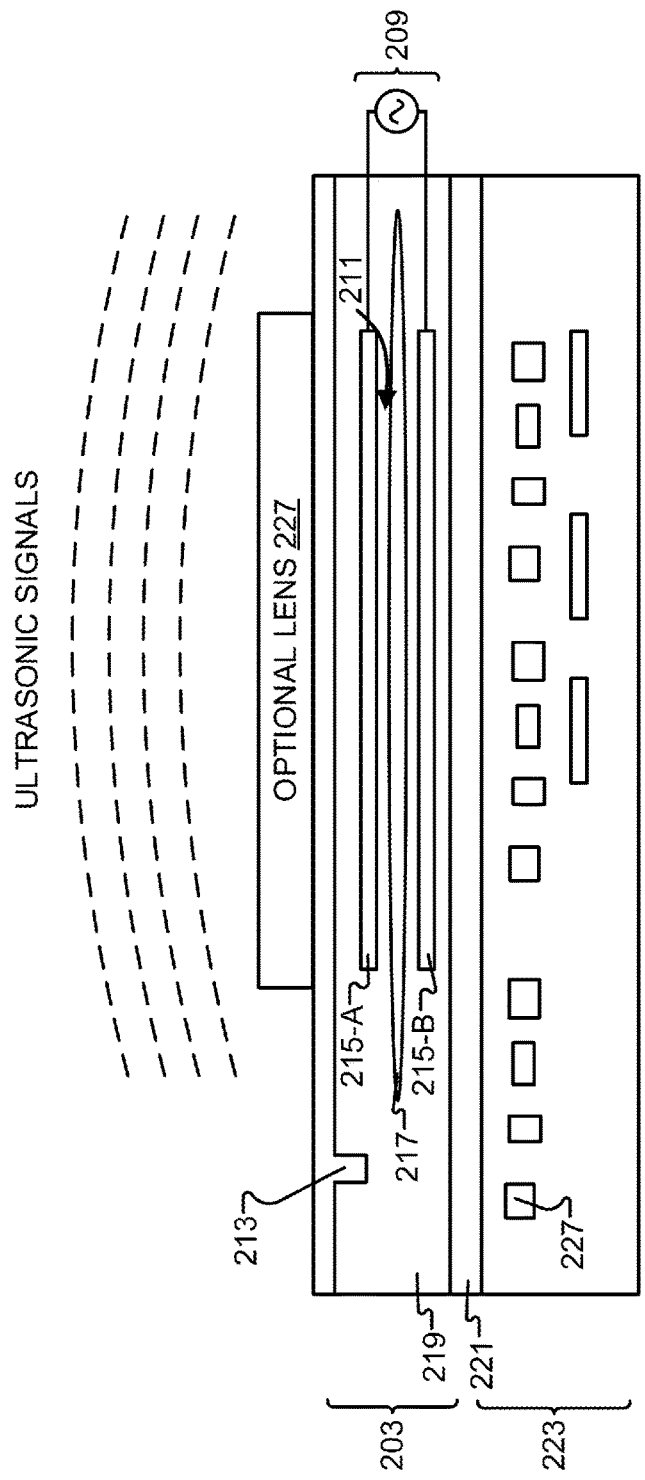
FIG. 2A illustrates a side view of a capacitive micromachined ultrasonic transducer device, in accordance with an embodiment of the disclosure.

MUTs work on electrostatic or piezoelectric principles, and are classified as capacitive type MUTs (CMUTs) or piezoelectric type MUTs (PMUTs), accordingly. Embodiments described herein focus on the use of CMUTs for ophthalmic applications. However, it is appreciated that PMUTs are equally suitable for the described embodiments and thus may be used alternatively or in combination to CMUTs. CMUTs are a type of microelectrical mechanical device in which a thin membrane (e.g., silicon, polysilicon, a metalized layer, electrode, or otherwise) is placed on top of a hollow cavity or space (e.g., as illustrated in FIG. 2A), which may be vacuum sealed. The cavity is disposed between the membrane and an electrode (e.g., formed from underlying Si that has been etched to form the cavity). A voltage (e.g., an alternating voltage) applied between the membrane and electrode may be utilized to vibrate the membrane to emit ultrasonic signals (e.g., energy in the form waves having a frequency based on the vibration of the membrane) that may be used for determining an accommodative effort of the eye of the user. Advantageously, CMUTs may be manufactured so as not to contain toxic materials (e.g., the CMUTs disclosed herein may contain silicon, variations of silicon compounds, and metals such as gold, platinum, titanium and others), which potentially simplifies device packaging and biocompatibility. Furthermore, the operating frequency of CMUTs is decoupled from the thickness of the transducer, meaning a transducer operating at a frequency of 5 MHz while maintaining a thickness of approximately ten microns may be able to fit inside a 0.8×0.8×0.8 mm 3 volume (e.g., to fit within an incision for implantation in an eye). Additionally, CMUTs can be optimized to operate at low voltage (e.g., less than 20 V), which is desirable for ophthalmic devices such as intraocular lens, contact lens, and other embodiments described herein. For these reasons, CMUTs (and other variants of MUTs) are advantageously utilized for ultrasonic sensing and emission in an ophthalmic device.

FIG. 1 illustrates exemplary placements of an ultrasonic transducer device 101 in an eye 100. Exemplary placements include a corneal placement (e.g., ultrasonic transducer device 101-A is placed within an accommodating contact lens 151 shaped or otherwise configured to be mounted on a cornea of the eye), a scleral placement (e.g., ultrasonic transducer device 101-B is implanted in or on the sclera of the eye in a subconjunctival position), and an intra-capsular placement (e.g., ultrasonic transducer devices 101-C and/or 101-D are placed within the capsular bag of the eye as part in an accommodating intraocular lens 153). It is appreciated that the placement of ultrasonic transducer device 101 illustrated in FIG. 1 is merely exemplary and should not be deemed limiting. Additionally, it is noted that in some embodiments, one or more ultrasonic transducer devices may be included within an ophthalmic device, meaning any one of or a combination of positions may be utilized. It is further appreciated that the techniques described below for one embodiment may be used in the other embodiments, in accordance with the teachings of the present disclosure.

In the accommodating contact lens 151, a CMUT can be made thin and flexible, so it is possible to integrate the CMUT in/on accommodating contact lens 151 (e.g., as ultrasonic transducer device 101-A). In many embodiments, it may be desirable for the transducer to be made thin for integration in a contact lens form factor (e.g., a thickness of 10 micrometers is possible for micromachined ultrasonic transducers). The CMUT may be placed in a CMUT array (e.g., a one dimensional linear array, a two-dimensional array, or otherwise). The array of transducers could be made flexible to better conform to the curvature of the cornea and/or accommodating contact lens 151. Contact lens 151 may direct or otherwise emit ultrasonic signals (e.g., as illustrated via dashed arrows in FIG. 1) towards the ciliary body, which is represented as the shaded part of eye 100. The outer layer (e.g., the ciliary epithelium) of the ciliary body includes ciliary processes, which may be displaced during an accommodative effort of the eye. When an individual changes (or attempts to change, in the case of patients with presbyopia) focus (e.g., when switching between near and distance vision) an accommodative effort occurs and the ciliary muscle constricts or relaxes to adjust a shape of the natural (or otherwise) lens of the eye. The accommodative effort may consequently result in displacement of various components included in the ciliary body (e.g., ciliary muscle, ciliary processes, and the like). Accordingly, the ultrasonic signals emitted by the ultrasonic transducer device 101 are directed towards the ciliary body (including the ciliary processes), which reflect the ultrasonic signals (e.g., as reflected ultrasonic signals) to determine the accommodative effort. Subsequently, the displacement (e.g., caused by the accommodative effort) may be determined through time of flight measurements (e.g., the time between emitting a pulse of the ultrasonic signal and receiving the associated pulse of the reflected ultrasonic signals). In some embodiments, a region of interest 107 corresponds to an edge of the ciliary body (e.g., where displacement may be more readily determined via the ultrasonic signals). Thus, it may be advantageous to target the ciliary processes (i.e., outer layer of the ciliary body) proximate to the edge of the ciliary body for measuring ciliary displacement in response to an accommodative effort. This is because the signal to noise ratio (e.g., relative to the reflected ultrasonic signals) may be lower for elements of the ciliary that are deeper within the ciliary body (e.g., the ciliary muscle) compared to the ciliary processes.

As illustrated in the accommodating contact lens 151, the ultrasonic transducer device 101 is not necessarily placed perpendicular to the ciliary body. Thus, in some embodiments, the ultrasonic signals may be directed or otherwise steered at a non-normal (relative to the planar surface of the ultrasonic transducer) angle. As will be discussed later, this angle may be achieved with acoustic lensing or digital beam forming using an array of ultrasonic transducers.

In the scleral embodiment, the CMUT can be placed in the sub-conjunctival space of the eye and mounted on or in the sclera (as depicted). In this embodiment, the size restriction for the CMUT may be relaxed relative to an intraocular lens, so that its linear dimensions (e.g., length and/or width) can increase to several millimeters. However, thickness of the ultrasonic transducer device 101-B may be kept below approximately 200 micrometers for comfort of the wearer. In this configuration, the relative alignment of the device to target the ciliary body may be less straightforward than for an intraocular implant (e.g., compared to placement of the ultrasonic transducer devices 101-C and 101-D within the capsular bag), as the ciliary body is not located directly in front or parallel to the ultrasonic transducer device 101. As stated above, one way of addressing this issue would be to use an acoustic lens to deflect the ultrasonic signals in the target direction or digital beam shaping to direct or steer the ultrasonic signals towards the ciliary body to obtain a signal (e.g., representative reflected ultrasonic signals received with the ultrasonic transducer device 101) with the highest signal to noise ratio (SNR). It is appreciated, that in some embodiments, the ultrasonic transducer device 101-B may be communicatively coupled (e.g., wired or wirelessly, such as wireless connection 109, which may use various wireless protocols such as IEEE 802.11) with accommodating contact lens 151, accommodating intraocular lens 153 and/or other external devices (not illustrated).

Specifics for the digital beam-shaping for some embodiments follow. The CMUT device may include a linear array of transducers, but the CMUT could also be a two dimensional array. A delay may be applied to the time of activation of individual transducers in the array that increases linearly as the element of the array gets closer to the limbus of the eye, so as to steer the acoustic energy (e.g., ultrasonic signals emitted by the ultrasonic transducer device 101) corresponding to an ultrasonic wavefront towards the ciliary body (e.g., when the ciliary body is not parallel to the axis of the array). On top of this linear delay, a quadratic modulation may be applied in some embodiments in order to adjust the focus of the ultrasonic wavefront (e.g., beam) to target the edge of the ciliary body (e.g., such as the edge of the ciliary body proximate to the limbus within the region of interest 107. Put another way, in the scleral configuration, contact lens configuration, or other variants described within embodiments of the disclosure, the ultrasonic signals emitted by the individual ultrasonic transducers in an array of transducers may be activated (e.g., as a pulse) out of phase with one another to form an ultrasonic wavefront that may be steered towards a target (e.g., any one of the constituents of the ciliary body, including the ciliary processes, and/or a combination thereof) in situations where the target is not parallel to the ultrasonic transducer device 101. In some embodiments, the individual transducers of the array closest to the limbus may emit energy last in order to properly aim the ultrasonic wavefront (e.g. beam) at the target. It is likely that patient-to-patient variability in anatomy, and slight variations in device placement will require individual calibration. Thus in some embodiments, the ultrasonic transducer device 101 may be able to scan the ultrasonic wavefront around and select a position and/or shape that provides a suitable SNR. This calibration may require the assistance of an external calibration device that provides additional power and/or control signals to the ultrasonic transducer device 101.

In the intra-capsular placement, displacement is measured via at least one of ultrasonic transducer device 101-C or ultrasonic transducer device 101-D as part of accommodating intraocular lens 153 disposed within the capsular bag. Accordingly, a CMUT transducer (e.g., ultrasonic transducer device 101-C and/or 101-D) could be placed on the edge of the accommodating intraocular lens 153 (see infra e.g., possible placements in FIG. 5B). Specifically, a (planar) surface of the ultrasonic transducer device 101 may be pointed towards the ciliary body (e.g., the ciliary processes), so that centripetal movement of the sphincter formed by the ciliary body may be detected. In some embodiments, the ultrasonic transducer device 101 may be placed anywhere between the edge of the capsular bag and approximately 2.25 mm away from the optical axis of the ophthalmic device (e.g., accommodating intraocular lens 153), so as to retain clear optical aperture that is at least 4.5 mm in diameter to avoid obstructing vision of eye 100. The region of interest 107 (e.g., the edge of the ciliary body formed by the ciliary muscle or processes) would then be located about 1-5 mm away from the ultrasonic transducer device 101, depending on placement of the ophthalmic device. Representative of an accommodative effort, the sphincter formed by the ciliary body is expected to move centripetally by approximately 300-500 micrometers in presbyopic and pseudophakic patients. Accordingly, in some embodiments the accommodating intraocular lens 153 may provide at least three (preferably five or more) degrees of accommodation which are adjusted based on the accommodative effort determined via the ophthalmic device sensing the displacement of the ciliary body. In order to distinguish how much displacement occurs, the ultrasonic transducer device 101 may have an axial resolution of at least 100 microns and, in some embodiments, have an axial resolution of at least 50 microns. To achieve this sensitivity, an operating frequency of the ultrasonic transducer device 101 in the range of 5-20 MHz may be chosen. In the same or other embodiments, an operating frequency of the ultrasonic transducer device 101 in the range of 10-40 MHz may be chosen to achieve the desired sensitivity. In order to provide robustness to lens wobble, two ultrasonic transducer devices 101 (e.g., ultrasonic transducer device 101-C and 101-D) could be placed diametrically opposed to one another on the ophthalmic device (e.g., as illustrated in FIG. 1 by accommodating intraocular lens 153 including ultrasonic transducer device 101-C and 101-D), in which case the differential signal obtained between the two may be used to determine the degree of displacement for the ciliary body related accommodative effort of the eye. In some embodiments a plurality of ultrasonic transducer devices (e.g., two, three, four, or more ultrasonic transducer devices) may be used collectively such that a combination of their output and/or received ultrasonic signals may be used (e.g., to detect ciliary displacement with increased signal to noise ratio), in accordance with the teachings of the present disclosure.

Figure 3:
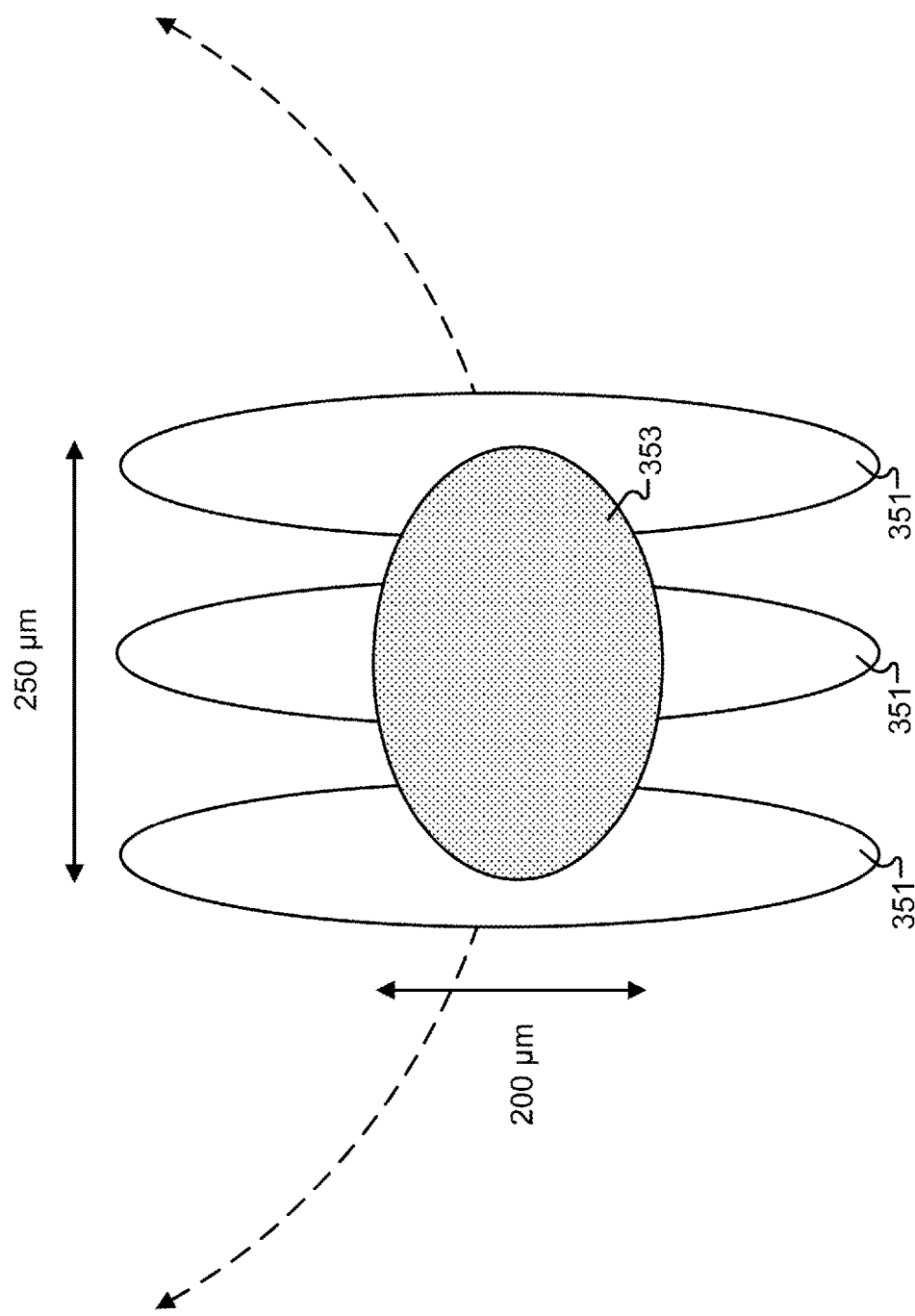
FIG. 3 illustrates an example ultrasonic wavefront incident on ciliary processes, in accordance with an embodiment of the disclosure.

The ciliary body includes ciliary processes which correspond to folds on the inner ciliary epithelium and appear as interdigitated finger-like structures. Without careful shaping of the ultrasonic wavefront or beam, it is possible that ultrasonic signals will be emitted between these processes in at least some ophthalmic devices following implantation or mounting. If this were the case, the ultrasonic transducer device 101 may then become unable to perform its function (e.g., SNR ratio is too low to meaningfully detect an amount of displacement of the ciliary body during an accommodation effort). In order to avoid this, the emitted ultrasonic signals (e.g., wavefront, beam, etc.) may be shaped so as to cover a minimal, elliptically-shaped area that is, in some embodiments, at least 200 micrometers wide and 250 micrometers tall when incident on the ciliary processes of the ciliary body (e.g., as illustrated in FIG. 3).

It is appreciated that in all the depicted embodiments, the ultrasonic signals may travel through one or more parts of the eye to reach the ciliary body or, more specifically, target constituents of the ciliary body within one or more regions of interest (e.g., region of interest 107). The ciliary body includes many ciliary processes as well as other components (e.g., ciliary muscle, vessels, fibrous connective tissue, epithelium including ciliary processes, and the like). Upon being incident on the ciliary body the ultrasonic signals may be reflected (e.g., as reflected ultrasonic signals) back to the ultrasonic transducer device 101. Accordingly, the ophthalmic devices, or more specifically ultrasonic transducer devices (e.g., ultrasonic transducer device 101) described in embodiments of the disclosure may be calibrated to distinguish between reflections from the ciliary body and other parts of the eye. Calibration may be unique to each user, since eye geometries differ between individuals. Moreover, calibration may require the ophthalmic device to be communicatively coupled with an external device.

Figure 2B:
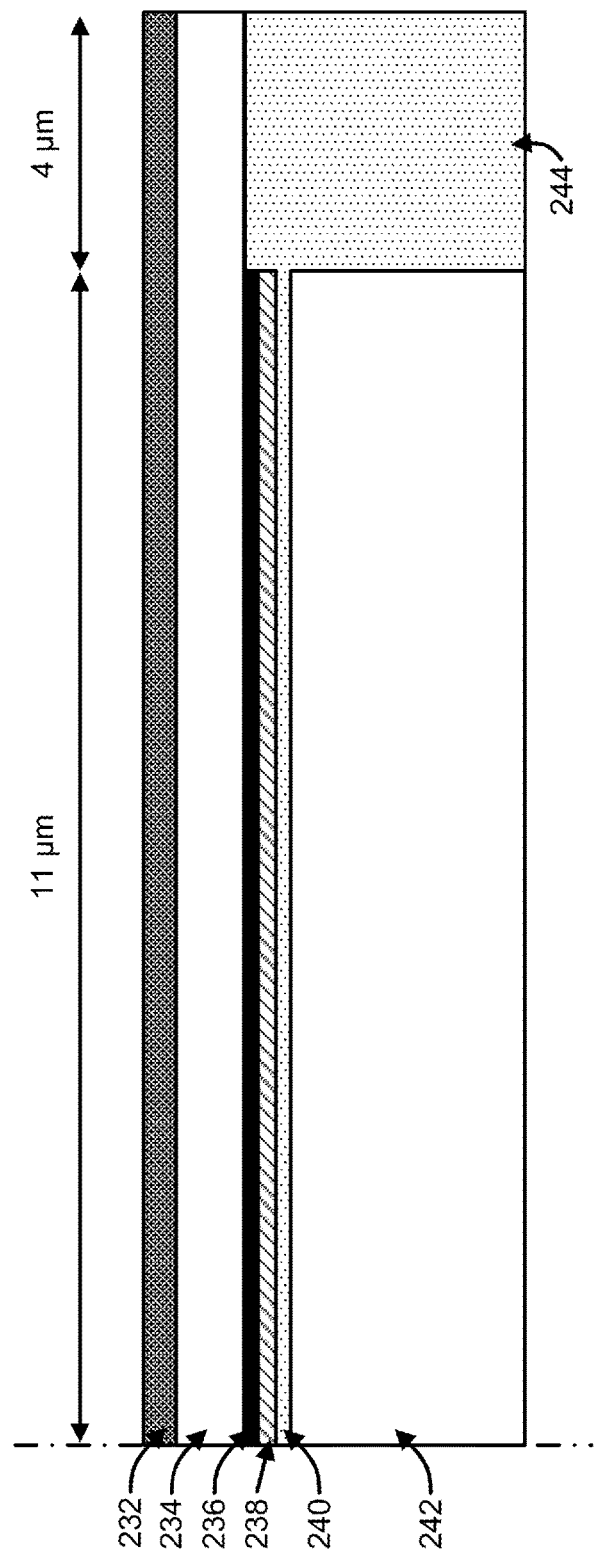
FIG. 2B illustrates a side view of a cell for a capacitive micromachined ultrasonic transducer device, in accordance with an embodiment of the disclosure.
Figure 4:
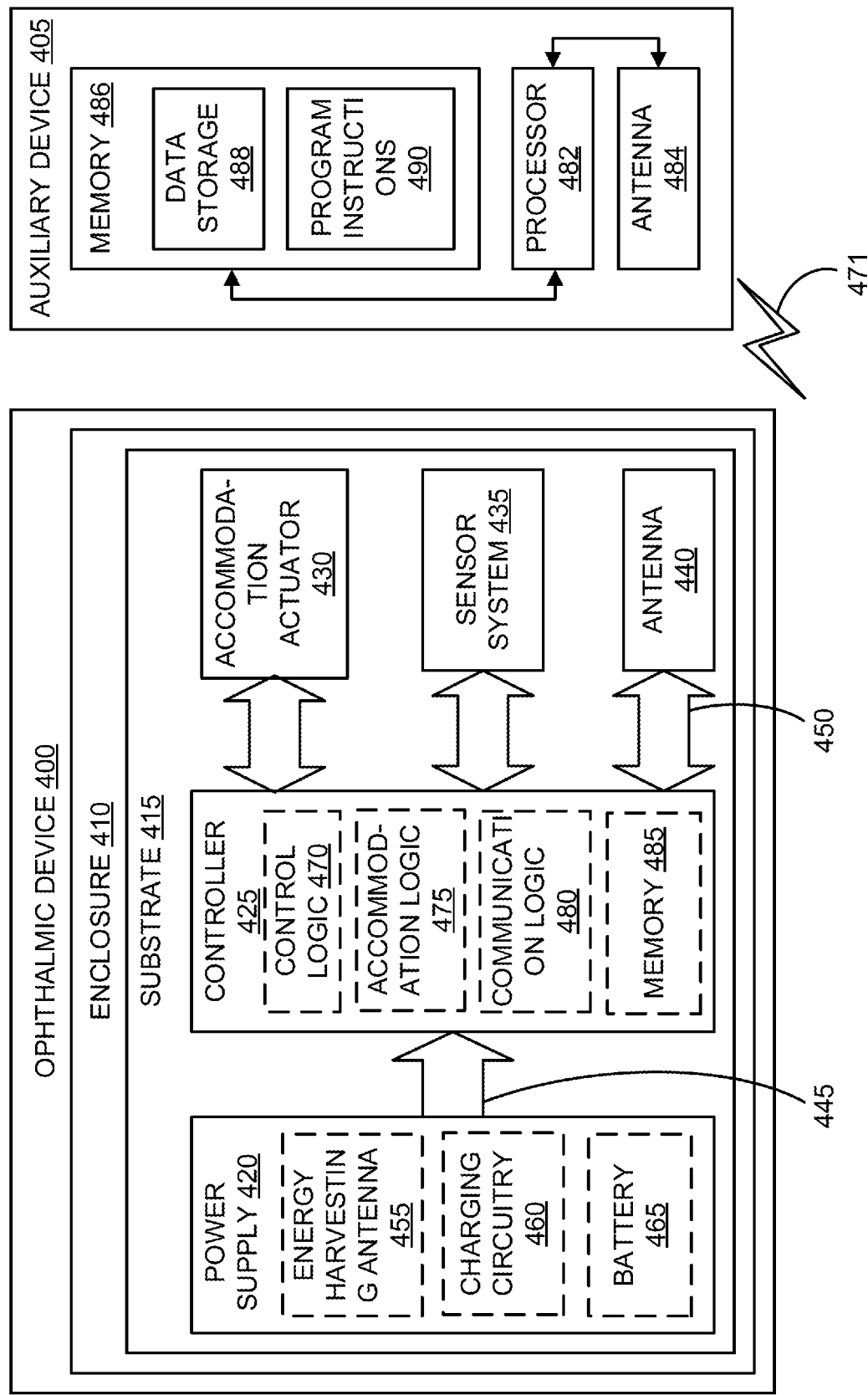
FIG. 4 illustrates a functional block diagram of an accommodating ophthalmic device including at least one ultrasonic transducer, in accordance with an embodiment of the disclosure.

FIG. 2A illustrates a side view of an example capacitive micromachined ultrasonic transducer (CMUT) device 201, in accordance with an embodiment of the disclosure. CMUT device 201 is one possible implementation of an ultrasonic transducer (e.g., ultrasonic transducer device 101 of FIG. 1) which may be implemented in various ophthalmic devices, systems, and or methods in accordance with embodiments of the disclosure. CMUT device 201 includes a cell 203 coupled to integrated circuit 223 (e.g., an application specific integrated circuit). The cell 203 includes membrane 211, cap 213 (to close off and seal the vacuum filled space 217), first electrode 215-A, second electrode 215-B, vacuum-filled space 217, substrate 219, and planarization layer 221 (e.g., to couple cell 203 with integrated circuit 223). Integrated circuit 223 may be coupled to cell 203 for controlling the emission of ultrasonic signals (or receiving, sensing, or otherwise measuring ultrasonic signals incident upon CMUT device 201). In one embodiment, membrane 211 includes first electrode 215-A. As shown, space 217 is disposed between first electrode 215-A and second electrode 215-B. A controller in the ophthalmic device (e.g., as illustrated in FIG. 2B, FIG. 4, or controlled locally via integrated circuit 223) may apply a voltage 209 across first electrode 215-A and second electrode 215-B (e.g., such as an alternating voltage) to adjust the size of the space 217 (e.g., via electrostatic attraction and repulsion between the electrodes in which the membrane 211 oscillates in accordance with the applied voltage) to generate (e.g., emit) ultrasonic signals. In some embodiments, there CMUT device 201 may include a plurality of cells 203, which may be arranged into a one or two dimensional array.

CMUT device 201 may have an active area of 1×1 mm, but ideally closer to 800×800 micrometers, possibly down to 500×500 micrometers. In one embodiment, CMUT device 201 includes one or more membranes, such as membrane 211 (e.g., the silicon that oscillates and is positioned between electrode 215-A and space 217) and one or more acoustic lenses (e.g., optional lens 227). The acoustic lens is packaged on top of the device that shapes the ultrasonic signals (e.g., wavefront or beam) to achieve the desired shape incident on the ciliary processes. In another embodiment, CMUT device 201 may include an array of controllable elements, each including one or more cells (e.g., cell 203), which may emit pulses of ultrasonic signals. The precise relative timing of activating emission of pulses of ultrasonic signals by each of the elements may then be adjusted for forming an ultrasonic wavefront (e.g., beam forming or steering). The ultrasonic wavefront may be dynamically steered and/or shaped and may provide a similar functionality as an acoustic lens that may be implemented in software/firmware of a controller rather than with an additional element on the device.

FIG. 2B illustrates a side view of cell 230 for a capacitive micromachined ultrasonic transducer device (e.g., CMUT device 201 illustrated in FIG. 2A), in accordance with an embodiment of the disclosure. In other words, cell 230 is one possible implementation of cell 203 illustrated in FIG. 2A. Referring back to FIG. 2B, cell 230 may be a cross section of a smallest repeat unit of an array of cells to form the CMUT device. The CMUT cell 230 includes electrode 232 (e.g., platinum, gold, titanium, other inert metals, or otherwise), a plate 234 (e.g., silicon, polysilicon, and the like), a vacuum-filled space 236, a nitride layer 238 (e.g., silicon nitride), an oxide layer 240 (e.g., silicon oxide), a bulk layer 242 (e.g., an underlying silicon substrate), and an insulating barrier 244 (e.g., pillar formed from silicon oxide).

CMUT cell 230 functions similarly as described in reference to FIG. 2A. In the illustrated embodiment of FIG. 2B, a voltage is applied between electrode 232 and a second electrode (e.g., corresponding to bulk layer 242 formed of conductive silicon) to cause electrostatic attraction and repulsion (e.g., due to an alternating voltage), which causes a membrane (e.g., plate 234) to oscillate or otherwise change the shape or volume of vacuum-filled space 236 resulting in emission of ultrasonic signals. Alternatively, in response to an incident ultrasonic signal or wavefront the membrane may move, which generates a voltage that may be measured (e.g., to sense or quantize reflected ultrasonic signals).

In the illustrated embodiment, the CMUT cell 230 is shaped to be part of an array of CMUT cells (e.g., to form a controllable element). A plurality of individually controllable elements may subsequently form an ultrasonic transducer device (e.g., CMUT 201 illustrated in FIG. 2A) having a total volume compatible for implantation into or on an eye (e.g., within a 1 mm² area). As illustrated in FIG. 2B, the CMUT cell 230 has an 11 μm radius (or diameter) with a 4 μm sidewall. The electrode 232 is 200 nm thick and formed from platinum. The plate 234 is 500 nm thick and formed from silicon or polysilicon. The vacuum-filled space 236 is 50 nm thick. The nitride layer 238 is 10 nm thick. The oxide layer 240 is 10 nm thick, and the bulk layer 242 is 10 μm thick and formed from silicon and may correspond to the bulk substrate upon which the CMUT cell 203 is formed. It is appreciated that specific dimensions are exemplary and should not be deemed limiting. Additionally, specific material compositions are also exemplary and that other compositions may be utilized while still functionally operating as a cell of an ultrasonic transducer.

Figure 2C:
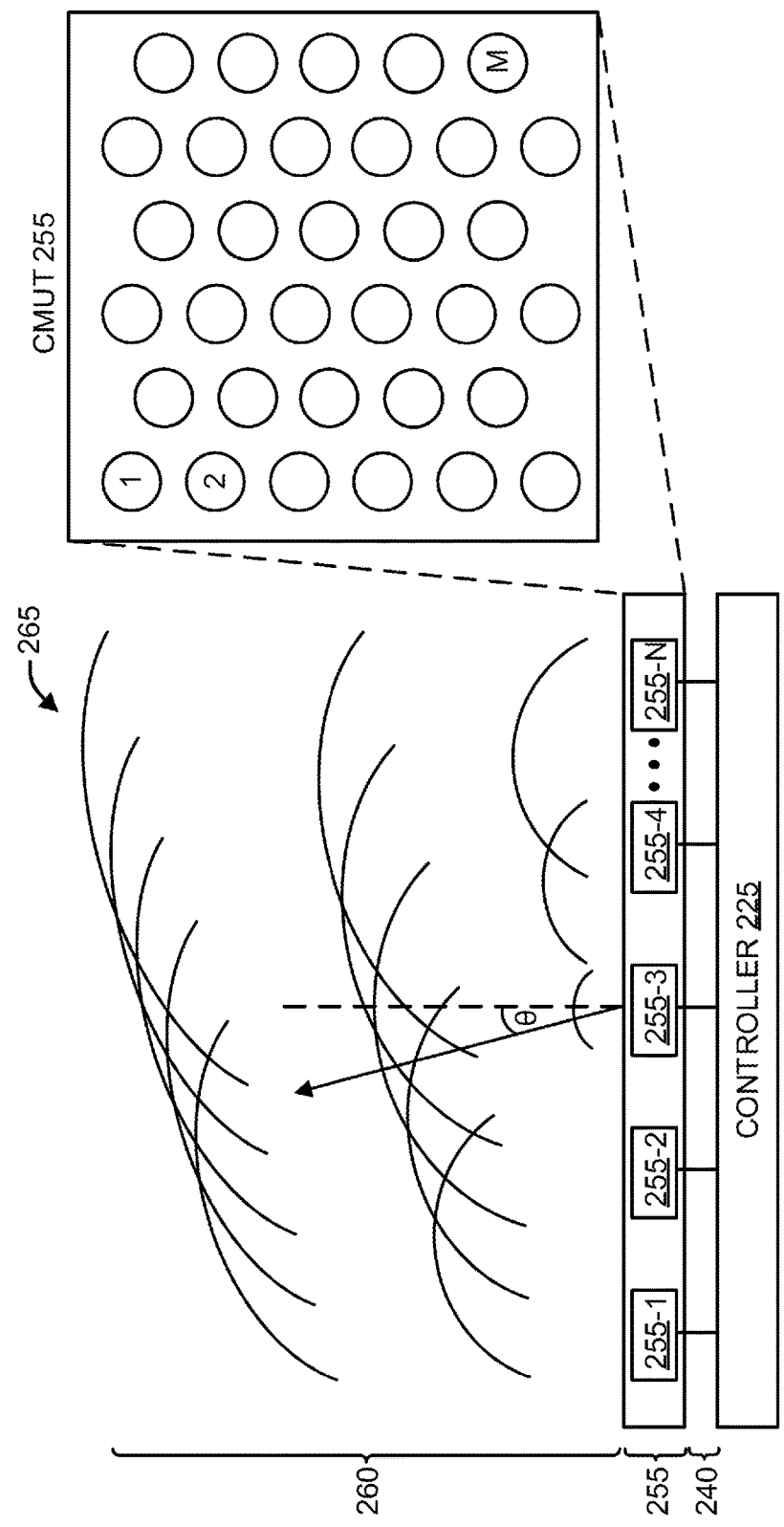
FIG. 2C illustrates an array of controllable elements with each of the controllable elements including an array of cells in a capacitive micromachined ultrasonic transducer device forming an ultrasonic wavefront, in accordance with an embodiment of the disclosure.

FIG. 2C illustrates a plurality of controllable elements 255 (e.g., 255-1, 255-2, . . . , 255-N) with each of the controllable elements including an array of cells (e.g., 255-N-1, 255-N-2, . . . , 255-N-M) in a capacitive micromachined ultrasonic transducer (CMUT) device 250 forming an ultrasonic wavefront 265, in accordance with an embodiment of the disclosure. As illustrated, each of the controllable elements of array 255 are individually coupled to controller 225 via a plurality of interconnects 240 for transmitting or receiving ultrasonic signals. In some embodiments, controller 225 may correspond to an integrated circuit directly bonded to array 255 (e.g., as illustrated in FIG. 2A), which is compatible with standard semiconductor processes (e.g., flip chip mounting). In other embodiments, controller 225 may be part of external circuitry (e.g., relative to array 255).

Each controllable element of CMUT 250 includes a two-dimensional array 250 of M circular cells (e.g., such as cell 230 illustrated in FIG. 2B) with hexagonal packing. However, it is appreciated that in other embodiments the cells may have a different shape (e.g., square, rectangle, hexagon, and the like) and a different packing arrangement (e.g., rectangular). Each cell is illustrated as having substantially the same size and shape within the array forming a single arrangement. However, it is appreciated that in some embodiments any one of, or a combination of cell sizes, shapes, and arrangements may be utilized.

CMUT device 250 is capable of forming an ultrasonic wavefront 265 that may be steered (e.g., to scan for the ciliary body and find a position or angle that provides a target or optimal SNR). Individually each of the controllable elements 255 may transmit and/or receive ultrasonic signals such that the CMUT device 250 may collectively form ultrasonic wavefront 265. In other words, each of the controllable elements 255 may be considered to be individual ultrasonic transducers that collectively form an ultrasonic transducer device (e.g., CMUT 250). Activating individual ultrasonic transducers (e.g., controllable element 255-1, 255-2, 255-3) included in the array 255 at different times to direct (e.g., at a non-normal angle relative to the planar surface of array 255). Rather than activating each of the individual elements 255 simultaneously, a delay (e.g., linear or otherwise) is utilized to form (and subsequently shape) ultrasonic wavefront 265. In the illustrated embodiment, pulses of ultrasonic signals/waves are emitted starting with controllable element 255-1 to 255-N to form the illustrated ultrasonic wavefront 265. The constructive and destructive interference from the individual interaction between ultrasonic signals emitted by the controllable elements and/or cells result in the formation of the wavefront. Thus, by adjusting the timing (e.g., as controlled by controller 255 or otherwise) of emitting the pulses of ultrasonic signals, the width of the pulses, and otherwise the ultrasonic wavefront 265 may be steered (e.g., to scan for an appropriate position and/or angle of the wavefront to be incident upon the ciliary body). For example, the individual controllable elements 255 and/or cells may be activated (i.e. pulsed) in series and sequentially with a fixed time delay between activation of consecutive cells such that there is a linear increase in delay. In a demonstrative embodiment that should be considered non-limiting, the time between element 255-1 and element 255-2 activating may be one time period, the time between element 255-1 and element 255-3 activating may be two time periods, the time between element 255-1 and element 255-4 activating may be three time periods, and so on such that the delay linear increases. In other embodiments a non-linear delay may be utilized (e.g., a quadratic modulation) to focus the ultrasonic wavefront 265. It is appreciated that different delays and activation schemes may be utilized to steer and/or focus the ultrasonic wavefront (e.g., to target the ciliary body for sensing ciliary displacement). It is further appreciated that ideal or target position/angle for the ultrasonic wavefront 265 to be incident upon the ciliary body is dependent on the relative arrangement of the CMUT device 250 with respect to the location of the ciliary body. Thus, the target position/angle (as dictated by the activation scheme/delay and the like) may be adjusted to appropriately position the ultrasonic wavefront 265.

FIG. 3 illustrates an example ultrasonic wavefront 353 incident on ciliary processes 351 of the ciliary body, in accordance with an embodiment of the disclosure. Ultrasonic wavefront 353 is one possible implementation of an ultrasonic wavefront emitted by an ultrasonic transducer device (e.g., ultrasonic wavefront 265 emitted by CMUT device 250 illustrated in FIG. 2C).

As shown in FIG. 3, a cross section of the ultrasonic wavefront (e.g., beam) spans multiple ciliary processes 351. Accordingly, beam 353 is large enough to be reflected by the ciliary processes 351 rather than passing between the individual ciliary processes 351 and not being reflected back to the ultrasonic transducer. In the illustrated embodiment, ultrasonic wavefront 353 has an elliptically-shape area that is at least 200 micrometers wide and 250 micrometers tall when incident upon the ciliary processes. In the illustrated embodiment, width refers to a direct substantially orthogonal to the longitudinal direction of the ciliary processes (e.g., the ciliary processes extend radially around pupil/lens of the eye as illustrated by the dashed arrow. It is appreciated that the specific dimensions of the ultrasonic wavefront 353 are merely demonstrative and that other dimensions may be used in accordance with embodiments of the disclosure.

FIG. 4 illustrates a functional block diagram of an accommodating ophthalmic device 400, in accordance with an embodiment of the disclosure. Ophthalmic device 400 may include the same or similar features as described in various embodiments of the disclosure (e.g., accommodating contact lens 151 and/or accommodating intraocular lens 153 illustrated in FIG. 1). Referring back to FIG. 4, an exposed portion of ophthalmic device 400 may include an enclosure 410 (e.g., formed from one or more materials) shaped to be contact-mounted to a corneal surface of an eye, disposed within the eye, or otherwise mounted in or on the eye. A substrate 415 may be embedded within or surrounded by enclosure 410 to provide a mounting surface for power supply 420, controller 425, accommodation actuator 430, sensor system 435, antenna 440, and various interconnects 445 and 450. The illustrated embodiment of power supply 420 includes an energy harvesting antenna 455, charging circuitry 460, and a battery 465. The illustrated embodiment of controller 425 includes control logic 470, accommodation logic 475, and communication logic 480. The illustrated embodiment of auxiliary device 405 includes a processor 482, an antenna 484, and memory 486. The illustrated embodiment of memory 486 includes data storage 488 and program instructions 490.

Controller 425 may be coupled to receive feedback control signals from sensor system 435 (which may include a CMUT device or other ultrasonic transducer to transmit and receive ultrasonic signals for determining ciliary displacement associated with an accommodative effort), and further coupled to operate accommodation actuator 430. Power supply 420 supplies operating voltages to the controller 425 and/or the accommodation actuator 430. Antenna 440 may be operated by the controller 425 to communicate information to and/or from ophthalmic device 400. In one embodiment, antenna 440, controller 425, power supply 420, and sensor system 435 are all situated on the embedded substrate 415. In one embodiment, accommodation actuator 430 may be embedded within enclosure 410, but is not disposed on substrate 415.

To facilitate contact-mounting (which is specific to the contact lens embodiment), the enclosure 410 may have a concave surface configured to adhere ("mount") to a moistened corneal surface (e.g., by capillary forces with a tear film coating the corneal surface). Additionally or alternatively, the ophthalmic device 400 may be adhered by a vacuum force between the corneal surface and enclosure 410 due to the concave curvature. While mounted with the concave surface against the eye, the outward-facing surface of the enclosure 410 may have a convex curvature that is formed to not interfere with eye-lid motion while the ophthalmic device 400 is mounted to the eye. For example, the enclosure 410 may be a substantially transparent curved disk shaped similarly to a contact lens.

Enclosure 410 may include one or more biocompatible materials, such as those employed for use in contact lenses or other ophthalmic applications involving direct contact with the corneal surface or inclusion in the capsular bag. Enclosure 410 may optionally be formed in part from such biocompatible materials or may include an outer coating with such biocompatible materials. Enclosure 410 may include materials configured to moisturize the corneal surface, such as hydrogels and the like. In some embodiments, enclosure 410 may include a deformable ("non-rigid") material to enhance comfort. In some instances, enclosure 410 may be shaped to provide a predetermined, vision-correcting optical power, such as can be provided by a contact lens. Enclosure material may be fabricated of various materials including a polymeric material, a hydrogel, PMMA, silicone based polymers (e.g., fluoro-silicon acrylate), other materials, or a combination thereof.

Substrate 415 includes one or more surfaces suitable for mounting or attaching the sensor system 435, controller 425, power supply 420, and antenna 440. Substrate 415 may be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennas, etc. In some embodiments, substantially transparent conductive materials (e.g., indium tin oxide) may be patterned on substrate 415 to form circuitry, electrodes, and the like. In one embodiment, antenna 440 may be formed by depositing a pattern of gold or another conductive material on substrate 415. Similarly, interconnects 445 and 450 may be formed by depositing suitable patterns of conductive materials on substrate 415. A combination of resists, masks, and deposition techniques may be employed to pattern materials on substrate 415. Substrate 415 may be a relatively rigid material, such as polyethylene terephthalate ("PET") or another material sufficient to structurally support the circuitry and/or electronics within enclosure 410. Ophthalmic device 400 may alternatively be arranged with a group of discrete substrates rather than a single substrate. For example, controller 425 and power supply 420 may be mounted to one substrate, while antenna 440 and sensor system 435 may be mounted to another substrate and the two may be electrically connected via interconnects.

In some embodiments, power supply 420 and controller 425 (and the substrate 415) may be positioned away from the center of ophthalmic device 400 and thereby avoid interference with light transmission to the eye through the center of ophthalmic device 400. In contrast, accommodation actuator 430 may be centrally positioned to apply optical accommodation (e.g., focus the light by adjust optical power) to the light transmitted to the eye through the center of ophthalmic device 400. For example, where ophthalmic device 400 is shaped as a concave-curved disk, substrate 415 may be embedded around the periphery (e.g., near the outer circumference) of the disk.

Substrate 415 may be shaped as a flattened ring with a radial width dimension sufficient to provide a mounting platform for the embedded electronics components. Substrate 415 may have a thickness sufficiently small to allow the substrate to be embedded in enclosure 410 without adversely influencing the profile of ophthalmic device 400. Substrate 415 may have a thickness sufficiently large to provide structural stability suitable for supporting the electronics mounted thereon. For example, substrate 415 may be shaped as a ring with a diameter of about 10 millimeters, a radial width of about 1 millimeter (e.g., an outer radius 1 millimeter larger than an inner radius), and a thickness of about 50 micrometers. Substrate 415 may optionally be aligned with the curvature of the eye-mounting surface of ophthalmic device 400 (e.g., convex surface). For example, substrate 415 may be shaped along the surface of an imaginary cone between two circular segments that define an inner radius and an outer radius. In such an example, the surface of substrate 415 along the surface of the imaginary cone defines an inclined surface that is approximately aligned with the curvature of the eye mounting surface at that radius. In some embodiments, ultrasonic transducers may be fabricated or otherwise disposed on substrate 415.

In the illustrated embodiment, power supply 420 includes a battery 465 to power the various embedded electronics, including controller 425. Battery 465 may be inductively charged by charging circuitry 460 and energy harvesting antenna 455. In one embodiment, antenna 440 and energy harvesting antenna 455 are independent antennae, which serve their respective functions of energy harvesting and communications. In another embodiment, energy harvesting antenna 455 and antenna 440 are the same physical antenna that are time shared for their respective functions of inductive charging and wireless communications with auxiliary device 405. Additionally or alternatively, power supply 420 may include a solar cell ("photovoltaic cell") to capture energy from incoming ultraviolet, visible, and/or infrared radiation. Furthermore, an inertial power scavenging system may be included to capture energy from ambient vibrations.

Charging circuitry 460 may include a rectifier/regulator to condition the captured energy for charging battery 465, or directly powering controller 425 without battery 465. Charging circuitry 460 may also include one or more energy storage devices to mitigate high frequency variations in energy harvesting antenna 455. For example, one or more energy storage devices (e.g., a capacitor, an inductor, etc.) may be connected to function as a low-pass filter.

Controller 425 contains logic to choreograph the operation of the other embedded components. Control logic 470 controls the general operation of ophthalmic device 400, including providing a logical user interface, power control functionality, etc. Accommodation logic 475 includes logic for monitoring feedback signals (e.g., reflected ultrasonic signals indicative of an accommodative effort) from sensor system 435 (and the ultrasonic transducers included therein), determining the current gaze distance of the user, and manipulating accommodation actuator 430 in response to provide the appropriate accommodation. The auto-accommodation may be implemented in real-time based upon feedback from the feedback signals, gaze tracking, or permit user control to select specific accommodation regimes (e.g., near-field accommodation for reading, far-field accommodation for regular activities, etc.). Circuitry of controller 425 may include, or couple to, a repository on substrate 415—as represented by the illustrative memory 485 (e.g., including non-volatile and/or volatile memory cells)—that, for example, is to store data written by such circuitry, data to determine operation of such circuitry and/or data received by (or to be sent from) ophthalmic device 400. Such a repository may store log information that describes performance of accommodation logic 475 and/or other components of controller 425.

Communication logic 480 provides communication protocols for wireless communication with auxiliary device 405 via antenna 440. In one embodiment, communication logic 480 provides backscatter communication via antenna 440 when in the presence of an electromagnetic field 471 output from auxiliary device 405. In one embodiment, communication logic 480 operates as a smart wireless radio-frequency identification ("RFID") tag that modulates the impedance of antenna 440 for backscatter wireless communications. The various logic modules of controller 425 may be implemented in software/firmware executed on a general purpose microprocessor, in hardware (e.g., one or more application specific integrated circuits), or a combination of both. Thus, in general, it is appreciated that the term "controller" used throughout the disclosure may include an individual controller (e.g., application specific integrated circuit, processor executing software/firmware, and the like), multiple components (e.g., multiple application specific integrated circuits, subcontrollers, other circuitry, and the like) working together to collectively function as a controller, or a combination thereof. In one embodiment, controller 425 may include a plurality of subcontrollers (e.g., application specific integrated controllers) each coupled to an individual ultrasonic transducer device to provide local control (e.g., ultrasonic transducer device 101-C and 101-D may each be locally controlled by respective subcontrollers). The subcontrollers may each be interconnected and/or coupled to a primary controller (e.g., an application specific integrated circuit, processor, or the like) to collectively form controller 425. In such a manner, individual tasks may be controlled by different subcontrollers or other components (e.g., one subcontroller may handle accommodation trigger while another subcontroller may handle ultrasonic signal transmission and/or sensing).

Ophthalmic device 400 may include various other embedded electronics and logic modules. For example, a light source or pixel array may be included to provide visible feedback to the user. An accelerometer or gyroscope may be included to provide positional, rotational, directional or acceleration feedback information to controller 425.

It is noted that the block diagram shown in FIG. 4 is described in connection with functional modules for convenience in description, but does not necessarily connote physical organization. Rather, embodiments of ophthalmic device 400 may be arranged with one or more of the functional modules ("sub-systems") implemented in a single chip, multiple chips, in one or more integrated circuits, or otherwise.

Auxiliary device 405 includes an antenna 484 (or group of more than one antennae) to send and receive wireless signals 471 to and from ophthalmic device 400. Auxiliary device 405 also includes a computing system with a processor 482 in communication with a memory 486. Memory 486 may be a non-transitory computer-readable medium that may include, without limitation, magnetic disks, optical disks, organic memory, and/or any other volatile (e.g., RAM) or non-volatile (e.g., ROM) storage system readable by the processor 482. Memory 486 may include a data storage 488 to store indications of data, such as data logs (e.g., user logs), program settings (e.g., to adjust behavior of ophthalmic device such as calibration), etc. Memory 486 may also include program instructions 490 for execution by processor 482 to cause the auxiliary device 405 to perform processes specified by the instructions 490. For example, program instructions 490 may cause auxiliary device 405 to provide a user interface that allows for retrieving information communicated from ophthalmic device 400 or allows transmitting information to ophthalmic device 400 to program or otherwise select operational modes of ophthalmic device 400. Auxiliary device 405 may also include one or more hardware components for operating antenna 484 to send and receive wireless signals 471 to and from one or both of ophthalmic device 400 and reference device.

Auxiliary device 405 may be a smart phone, digital assistant, or other portable computing device with wireless connectivity sufficient to provide the wireless communication link 471. Auxiliary device 405 may also be implemented as an antenna module that may be plugged in to a portable computing device, such as in an example where the communication link 471 operates at carrier frequencies not commonly employed in portable computing devices. In some instances, auxiliary device 405 is a special-purpose device configured to be worn relatively near a wearer's eye to allow the wireless communication link 471 to operate with a low power budget. For example, the auxiliary device 405 may be integrated in a piece of jewelry such as a necklace, earing, etc. or integrated in an article of clothing worn near the head, such as a hat, headband, etc. In other embodiments, auxiliary device 405 is a personal computer or game console.

FIGS. 5A & 5B illustrate an accommodating intraocular lens (e.g., one possible implementation of ophthalmic device 400 in FIG. 4), in accordance with an embodiment of the disclosure. The accommodating intraocular lens depicted in FIGS. 5A & 5B may include any of the features described in connection with the ophthalmic device 400 shown in FIG. 4 and/or other embodiments disclosed herein.

FIG. 5A shows a cross-sectional illustration of an eye 500 having implanted therein an intraocular device 553 that, according to an embodiment, determines a direction of gaze, an accommodative effort, or the like based on ultrasonic measurement of ciliary displacement. Intraocular device 553 is disposed within the capsular bag of eye 500 and may include at least one ultrasonic transducer device 501 to measure the movement of the ciliary body (e.g., ciliary processes) by calculating a time of flight of the ultrasonic signals.

FIG. 5B is a more detailed view of accommodating intraocular lens 553 illustrated in FIG. 5A, with several exemplary implementations (e.g., placement) of ultrasonic transducer devices 501 (e.g., CMUTs or otherwise), in accordance with an embodiment of the disclosure. As shown, accommodating intraocular lens 553 includes haptics 561 (to position accommodating intraocular lens 553 inside eye 500 and to resist movement within the capsular bag), accommodation actuator 530 (e.g., including a lens coupled to a dynamic optical to provide variable focus/adjustable optical power), power supply 520 (e.g., a battery, an RF coupled antenna, or the like), controller 525 (e.g., application specific integrated circuit), and housing 561 (e.g., an enclosure formed of one or more materials such as hydrogels, silicones, among others). As shown, ultrasonic transducer device (e.g., 501-A, 501-B, and 501-C) can be placed anywhere on, or even remote from, accommodating intraocular lens 553 (e.g., as illustrated in FIG. 1 by ultrasonic transducer device 101-B). As shown, ultrasonic transducer device 501-A may be remote from accommodating intraocular lens 553 and coupled to the accommodating intraocular lens 553 via wires or wirelessly. Ultrasonic transducer device 501-A may be secured separately inside eye 500. Ultrasonic transducer device 501-B may be placed on one or both haptics 561. Similarly ultrasonic transducer device 501-C may be placed on or in housing 561 (e.g., on one or both sides of housing 561).

The illustrated embodiment of accommodating intraocular lens 553 includes housing 561 and circuitry disposed therein. An exterior of accommodating intraocular lens 553 may include a surface of housing 561 that is biocompatible to accommodate direct contact with an interior of a human (or other) eye. Such a surface of housing 561 may be formed by one or more materials that are biocompatible to accommodate implantation of accommodating intraocular lens 553. Examples of such materials include, but are not limited to, any of various biocompatible hydrogels, silicones, hydrophobic acrylics, fluorinated polymethacrylates, and/or the like. In one embodiment, housing 561 includes a coating of biocompatible material that, for example, is formed by atomic layer deposition. Such materials may be adapted from those used in existing intraocular devices, for example.

Figure 6A:
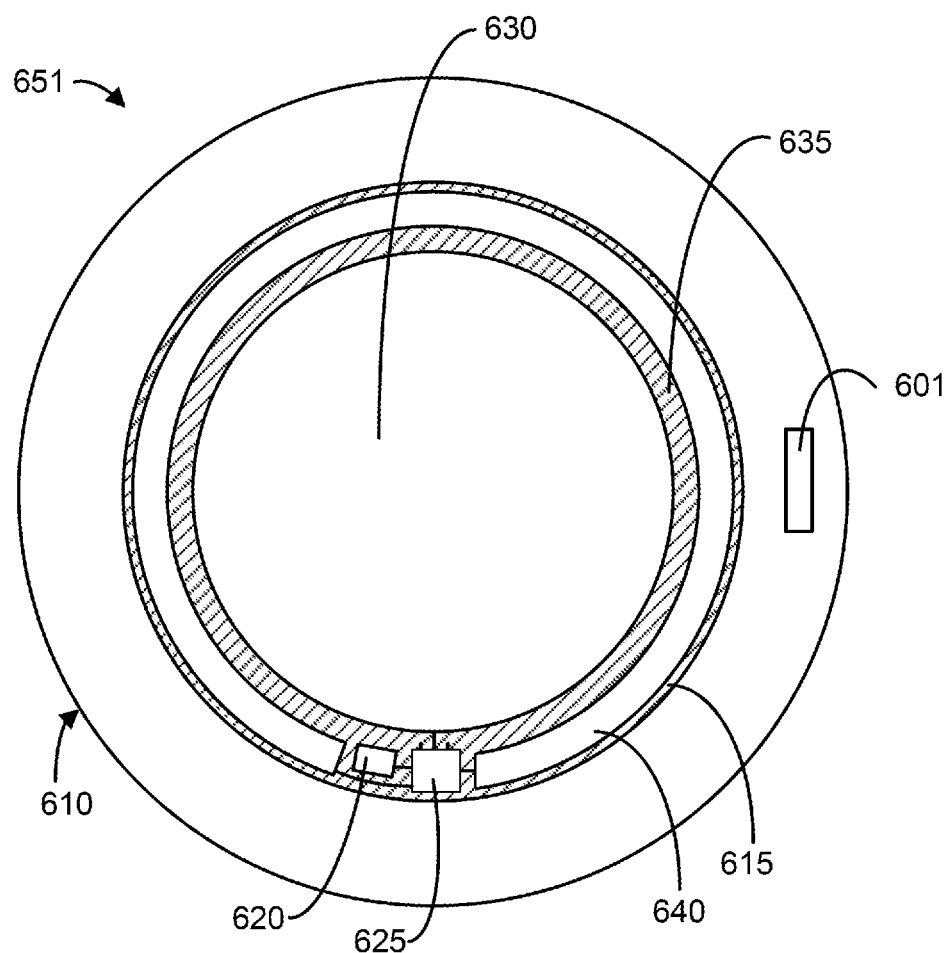
FIGS. 6A & 6B illustrate an eye-mountable device, in accordance with an embodiment of the disclosure.
Figure 6B:
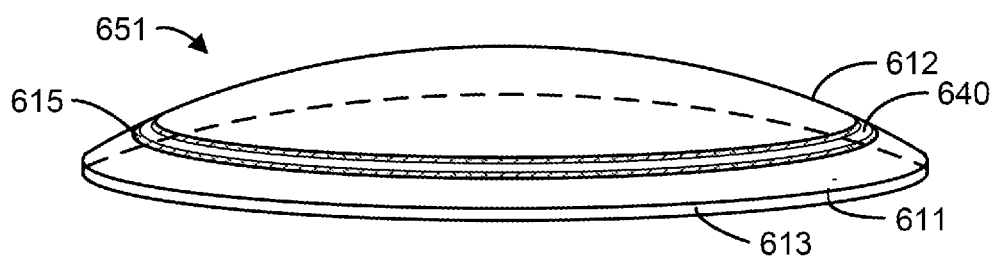

FIGS. 6A and 6B illustrate two views of an eye-mountable device 651 (e.g., a contact lens), in accordance with an embodiment of the disclosure. Eye-mountable device 651 is one possible implementation of ophthalmic device 400 illustrated in FIG. 4. FIG. 6A is a top view of eye-mountable device 651 while FIG. 6B is a perspective view of the same. The illustrated embodiment of eye-mountable device 651 includes an enclosure 610, substrate 615, power supply 620, controller 625, accommodation actuator 630, ultrasonic transducer device 601 (e.g., a CMUT device disposed in enclosure 610), and an antenna 640. It is appreciated that eye-mountable device 651 may include the same or similar features of the various embodiments of the disclosure.

Enclosure 610 of eye-mountable device 651 may be shaped as a curved disk. Enclosure 610 is a substantially transparent material to allow incident light to be transmitted when the eye while eye-mountable device 651 is mounted to the eye. Enclosure 610 may include one or more biocompatible materials similar to those employed to form vision correction and/or cosmetic contact lenses in optometry, such as a polymeric material, polyethylene terephthalate ("PET"), polymethyl methacrylate ("PMMA"), polyhydroxyethylmethacrylate ("polyHEMA"), a hydrogel, silicon based polymers (e.g., fluoro-silicon acrylate), combinations of these, or otherwise. Enclosure 610 may be formed with one side having a concave surface 611 suitable to fit over a corneal surface of the eye. The opposite side of the disk may have a convex surface 612 that does not interfere with eyelid motion while eye-mountable device 651 is mounted to the eye. In the illustrated embodiment, a circular or oval outer side edge 613 connects the concave surface 611 and convex surface 612.

Eye-mountable device 651 may have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of eye-mountable device 651 may be selected according to the size and/or shape of the corneal surface of the wearer's eye. Enclosure 610 may be formed with a curved shape in a variety of ways. For example, techniques similar to those employed to form vision-correction contact lenses, such as heat molding, injection molding, spin casting, etc., may be employed to form enclosure material 610.

Substrate 615 may be embedded within enclosure 610. Substrate 615 may be embedded to be situated along the outer periphery of enclosure 610, away from the central region where accommodation actuator 630 is positioned. In the illustrated embodiment, substrate 615 encircles accommodation actuator 630. Substrate 615 may not interfere with vision because it is too close to the eye to be in focus and is positioned away from the central region where incident light is transmitted to the light-sensing portions of the eye. In some embodiments, substrate 615 may optionally be formed of a transparent material to further mitigate effects on visual perception. Substrate 615 may be shaped as a flat, circular ring (e.g., a disk with a centered hole). The flat surface of substrate 615 (e.g., along the radial width) may be a platform for mounting electronics and for patterning conductive materials to form electrodes, antennas, and/or interconnections.

Ultrasonic transducer device 601 may emit and sense ultrasonic signals. However, in some embodiments there may be dedicated ultrasonic emitters and receivers. Ultrasonic transducer device 601 may be used to determine an amount of ciliary displacement (e.g., contraction of the ciliary processes) in the eye representative of an accommodative effort, as discussed elsewhere in this disclosure.

Accommodation actuator 630 may be centrally positioned within enclosure 610 to affect the optical power of eye-mountable device 651 in the user's center of vision. In various embodiments, accommodation actuator 630 operates by changing its index of refraction under the influence of controller 625. By changing its refractive index, the net optical power of the curved surfaces of eye-mountable device 651 may be altered, thereby applying controllable accommodation. Accommodation actuator 630 may be implemented using a variety of different electro-active optical devices. For example, accommodation actuator 630 may be implemented using a layer of liquid crystal (e.g., a liquid crystal cell) disposed in the center of enclosure 610. In other embodiments, accommodation actuator 630 may be implemented using other types of electro-active optical materials such as electro-optic materials that vary refractive index in the presence of an applied electric field. Accommodation actuator 630 may be a distinct device embedded within enclosure 610 (e.g., liquid crystal cell), a bulk material having a controllable refractive index, or a material having controllable shape (e.g. liquid lens or electroactive polymer). In yet another embodiment, accommodation actuator 630 may be implemented using a deformable lens structure that changes shape under the influence of an electrical signal. Accordingly, the optical power of eye-mountable device 651 may be controlled by controller 625 with the application of electric signals via one or more electrodes extending from controller 625 to accommodation actuator 630.

Accommodation actuator 630 may be implemented using a variety of different liquid crystal structures including nematic liquid crystal, nematic twisted liquid crystal, cholesteric liquid crystal, or blue phase liquid crystal. Since a low switching voltage is desirable for low power chip design, nematic liquid crystals with switching voltages less than 5 V are suitable. With the application of a 5V control signal, refractive index switching ranging from approximately 1.74 in an off-mode to 1.52 in an on-mode is achievable. A refractive index shift of 0.2 should be sufficient to provide near-field accommodation for reading. It is appreciated that embodiments of accommodation actuator 630 described in relation to eye-mountable device 651 may also be implemented in other ophthalmic devices, such as an accommodating intraocular lens as illustrated and described in the disclosure.

Returning to FIG. 6A, loop antenna 640 is a layer of conductive material patterned along the flat surface of the substrate to form a flat conductive ring. In some embodiments, to allow additional flexibility along the curvature of the enclosure material, loop antenna 640 may include multiple substantially concentric sections electrically joined together. Each section may then flex independently along the concave/convex curvature of eye-mountable device 651. In the same or other embodiments, loop antenna 640 may be formed without making a complete loop. For instance, antenna 640 may have a cutout to allow room for controller 625 and power supply 620, as illustrated in FIG. 6A. However, loop antenna 640 may also be arranged as a continuous strip of conductive material that wraps entirely around the flat surface of substrate 615 one or more times. For example, a strip of conductive material with multiple windings may be patterned on the backside of substrate 615 opposite controller 625, and power supply 620. Interconnects between the ends of such a wound antenna (e.g., the antenna leads) may then be passed through substrate 615 to controller 625.

Figure 7:
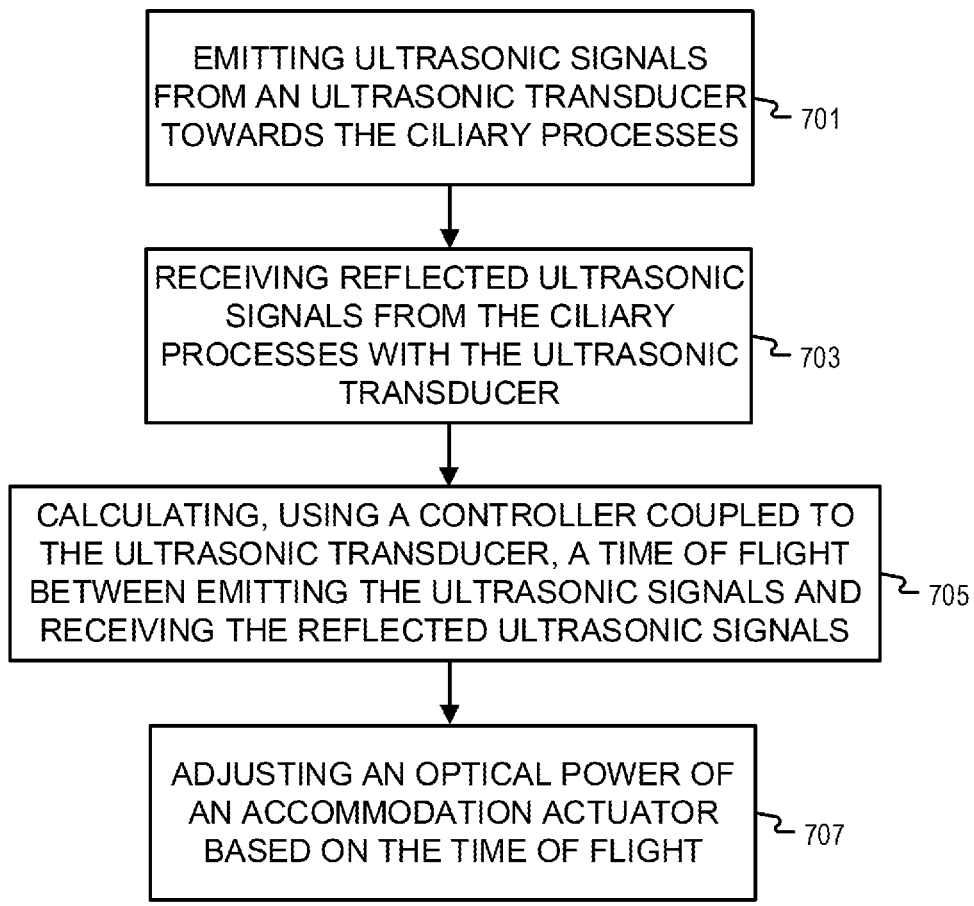
FIG. 7 illustrates an example method of measuring a location of ciliary processes in an eye, in accordance with an embodiment of the disclosure.

FIG. 7 illustrates an example method 700 of measuring a location of ciliary processes in an eye, in accordance with an embodiment of the disclosure. Blocks 701-707 in method 700 may occur in any order and even in parallel. Moreover, one of ordinary skill in the art will appreciate that blocks may be added to or removed from method 700 in accordance with the teachings of the present disclosure. It is appreciated that while method 700 is directed to ciliary processes (e.g., within the epithelium of the ciliary body), method 700 is also applicable to other constituents of the ciliary body (or otherwise) for measuring ciliary displacement to determine a level of accommodative effort. In some embodiments, method 700 may be used in conjunction with an ophthalmic device (e.g., ophthalmic device 400 illustrated in FIG. 4 and/or any other ophthalmic device described in the various embodiments of the disclosure, such as a contact lens, an intraocular lens, an intraocular implant, or other ophthalmic device) for providing accommodation (e.g., in place of, or in combination with, a lens of the eye).

Block 701 shows emitting ultrasonic signals from an ultrasonic transducer device towards the ciliary processes. In some embodiments this may include applying a voltage across a first electrode and a second electrode in a CMUT (or other ultrasonic transducer device) to adjust the size of a vacuum-filled space and emit the ultrasonic signals. It is appreciated that the width of the ultrasonic signals may span more than one ciliary process in the ciliary processes.

Block 703 illustrates receiving reflected ultrasonic signals from the ciliary processes with the ultrasonic transducer. In some embodiments this may include measuring a voltage change across the electrodes in the CMUT device when the membrane of the CMUT device vibrates in response to receiving the reflected ultrasonic signals.

Block 705 depicts calculating, using a controller coupled to the ultrasonic transducer, a time of flight between emitting the ultrasonic signals and receiving the reflected ultrasonic signals. In some embodiments, the controller includes an oscillator or other device to record the time between emission and receipt of the pulses of ultrasonic signals to calculate ciliary displacement (e.g., changes in shape/position of the ciliary processes or otherwise which are indicative of accommodative effort). The time of flight may determine the level of contraction or relaxation (e.g., the location of) of the ciliary processes resultant of accommodative effort. It is appreciated that the location is one location in a plurality of discrete locations (e.g., the location associated with 20% contraction, 40% contraction, 60% contraction, 80% contraction, and 100% contraction of the ciliary muscle as well as corresponding relaxation). It is appreciated that a controller (e.g., controller 425 illustrated in FIG. 4) may round to the nearest discrete location of the ciliary displacement to associate different levels of accommodative effort and adjust accommodation provided by the ophthalmic device, accordingly. In some embodiments, in addition to, or in lieu of, measuring the ciliary displacement (e.g., change in ciliary position associated with a level of contraction or relaxation of the ciliary muscle or body), a velocity or change in velocity may be utilized to determine the level of accommodative effort. For example, velocity of the ciliary displacement may be obtained from differences between time of flight measurements and subsequently utilized to determine the level of accommodative effort (e.g., a first velocity may be associated with a first level of accommodative effort, a second velocity may be associated with a second level of accommodative effort, and so on).

Block 707 shows adjusting an optical power of an accommodation actuator based on the time of flight. In some embodiments this may include applying a voltage across a liquid crystal device to adjust the optical power of the accommodation actuator based on the level of contraction of muscles in the eye. Depending on the level of accommodative effort (e.g., indicated by a degree of ciliary displacement such as contraction of the ciliary muscle), the accommodation actuator may have two or more discrete levels of focus/optical power (e.g., one mode for each 20% of contraction).

Figure 8:
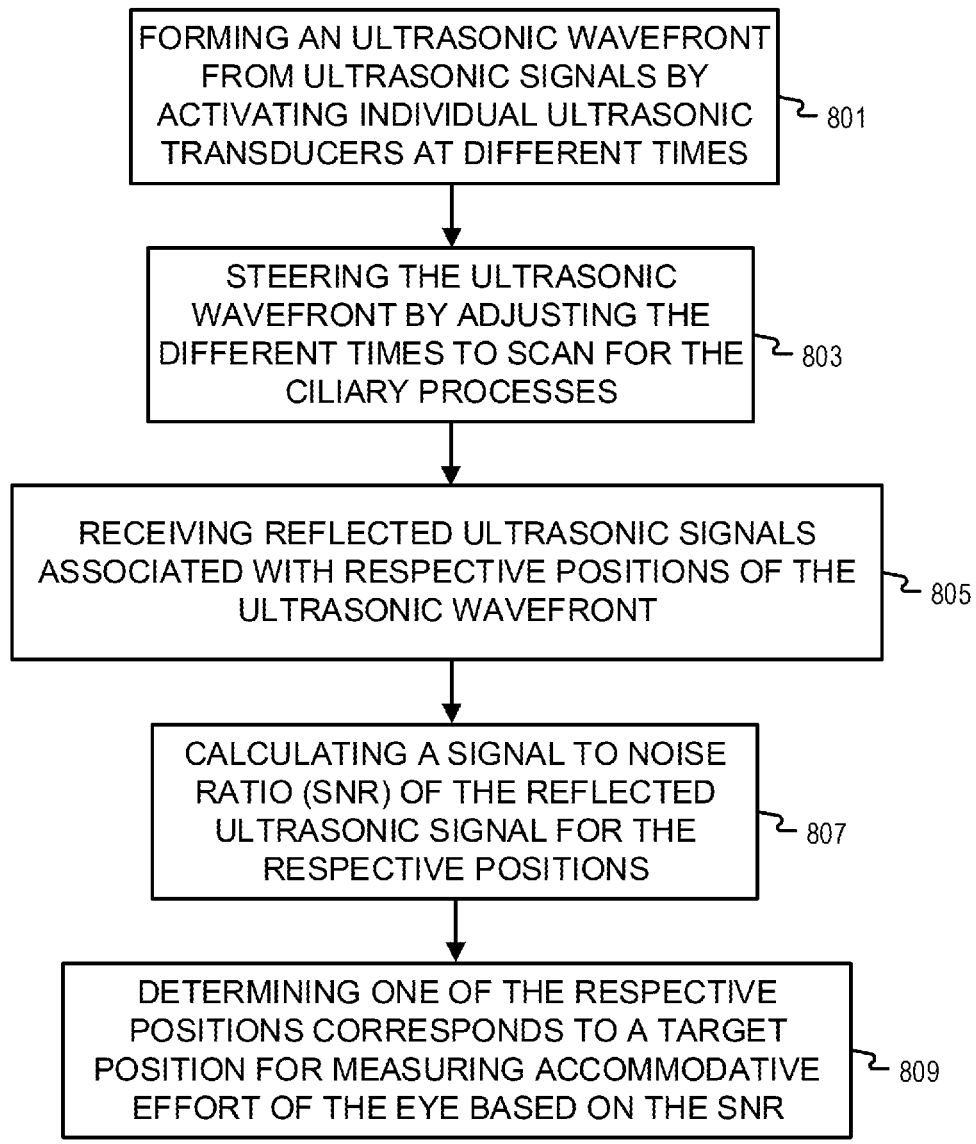
FIG. 8 illustrates an example method for determining a target position of an ultrasonic wavefront for measuring accommodative effort of the eye, in accordance with an embodiment of the disclosure.

FIG. 8 illustrates an example method 800 for determining a target position of an ultrasonic wavefront for measuring accommodative effort of the eye, in accordance with an embodiment of the disclosure. Blocks 801-809 in method 800 may occur in any order and even in parallel. Moreover, one of ordinary skill in the art will appreciate that blocks may be added to or removed from method 800 in accordance with the teachings of the present disclosure. It is appreciated that while method 800 is directed to ciliary processes (e.g., within the epithelium of the ciliary body), method 800 is also applicable to other constituents of the ciliary body (or otherwise) for steering an ultrasonic wavefront to measure ciliary displacement to indicative of a level of accommodative effort. In some embodiments, method 800 may be used in conjunction with an ophthalmic device (e.g., ophthalmic device 400 illustrated in FIG. 4 and/or any other ophthalmic device described in the various embodiments of the disclosure, such as a contact lens, an intraocular lens, an intraocular implant, or other ophthalmic device) for providing accommodation (e.g., in place of, or in combination with, a lens of the eye).

Block 801 illustrates forming an ultrasonic wavefront from ultrasonic signals by activating individual ultrasonic transducers (e.g., included in a plurality of micromachined ultrasonic transducer devices) at different times (or a same time when directing the ultrasonic wavefront perpendicular to the ultrasonic transducer device). The individual ultrasonic transducers may be activated (e.g., to emit a pulse of ultrasonic signals) in series and out of phase (e.g., as described in relation to FIG. 2C) to form an ultrasonic wavefront due to constructive and destructive interference.

Block 803 shows steering the ultrasonic wavefront by adjusting the different times (e.g., delay of activation) to scan for the ciliary body (e.g., ciliary processes). A controller may raster the ultrasonic wavefront along a range of positions. For example, the planar cross-section of the ultrasonic wavefront may be able to be steered from up to a 3 degree angle, 10 degree angle, 20 degree angle, 30 degree angle, or other angles relative to the normal direction of a planar surface of the ultrasonic transducer device. The different times may be adjusted to control the timing and/or order that the individual elements (or cells) of the ultrasonic transducer device emits pulses of ultrasonic signals to steer the ultrasonic wavefront to different positions (e.g., to scan for the ciliary body).

Block 805 illustrates receiving the reflected ultrasonic signals associated with respective positions the ultrasonic wavefront is steered. In other words a map of the range of positions the ultrasonic wavefront is scanned and the resultant reflected ultrasonic signal is determined. The relationship between the ultrasonic wavefront position and received reflected ultrasonic signals may be stored (e.g., in a table, array, or otherwise).

Block 807 shows calculating a signal to noise ratio (SNR) of the reflected ultrasonic signal for each of the respective positions. In one embodiment, the amplitude of the reflected ultrasonic signal relative to the noise of the ultrasonic transducer (or individual cell) may be determined (e.g., by calculating a difference between the amplitude and the noise).

Block 809 shows determining at least one of the respective positions corresponds to a target position (e.g., the location of the ciliary body, processes, or otherwise) based on the SNR. In one embodiment, a controller may determine the highest SNR value may and associated wavefront position is the target position of the ultrasonic wavefront. In other embodiments, the edge of the ciliary body may be determined via the ultrasonic wavefront steering/rastering while an individual changes focus to determine a range of ultrasonic wavefront positions that may be collectively used to determine ciliary displacement in response to accommodative effort.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, embodiments of the present disclosure such as an ophthalmic device, contact lens, intraocular lens, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. At least one non-transitory machine-accessible storage medium that provides instructions that, when executed by a machine, will cause the machine to perform operations comprising:
   emitting ultrasonic signals from an ultrasonic transducer towards ciliary processes in an eye, wherein a width of the ultrasonic signals spans more than one ciliary process included in the ciliary processes;
   receiving reflected ultrasonic signals from the ciliary processes with the ultrasonic transducer;
   calculating a first time of flight between emitting the ultrasonic signals and receiving the reflected ultrasonic signals; and
   adjusting an optical power of an accommodation actuator based on the first time of flight.

2. The at least one non-transitory machine-accessible storage medium of claim 1, that provides additional instructions that, when executed by the machine, will cause the machine to perform further operations comprising:
   emitting second ultrasonic signals from the ultrasonic transducer towards the ciliary processes in the eye;
   receiving second reflected ultrasonic signals from the ciliary processes with the ultrasonic transducer;
   calculating a second time of flight between emitting the second ultrasonic signals and receiving the second reflected ultrasonic signals; and
   determining a velocity of ciliary displacement based on first time of flight and the second time of flight, and wherein the optical power of the accommodation actuator is adjusted based, at least in part, on the velocity.

3. The at least one non-transitory machine-accessible storage medium of claim 1, that provides additional instructions that, when executed by the machine, will cause the machine to perform further operations comprising:
   performing multiple instances of the emitting the ultrasonic signals and the receiving the reflected ultrasonic signals in response; and
   calculating multiple times of flights, including the first time of flight, each indicative of a duration between the emitting the ultrasonic signals and the receiving the reflected ultrasonic signals for a corresponding one of the multiple instances; and calculating a change in velocity of ciliary displacement based on the multiple time of flights, wherein the optical power of the accommodation actuator is adjusted, at least in part, based on the change in velocity.

4. The at least one non-transitory machine-accessible storage medium of claim 1, providing additional instructions that, when executed by the machine, will cause the machine to perform further operations, comprising:
   directing the ultrasonic signals in a non-normal direction relative to the ultrasonic transducer.

5. The at least one non-transitory machine-accessible storage medium of claim 4, wherein directing includes using at least one of an acoustic lens disposed on the ultrasonic transducer or a plurality of ultrasonic transducers including the ultrasonic transducer.

6. The at least one non-transitory machine-accessible storage medium of claim 5, providing additional instructions that, when executed by the machine, will cause the machine to perform further operations, comprising:
   forming an ultrasonic wavefront from the ultrasonic signals by activating individual ultrasonic transducers included in the plurality of ultrasonic transducers at different times to direct the ultrasonic wavefront towards the ciliary processes.

7. The at least one non-transitory machine-accessible storage medium of claim 5, providing additional instructions that, when executed by the machine, will cause the machine to perform further operations, comprising:
   steering an ultrasonic wavefront formed by the ultrasonic signals by activating individual ultrasonic transducers included in the plurality of ultrasonic transducers at different times to scan for the ciliary processes;
   calculating a signal to noise ratio (SNR) of the reflected ultrasonic signals for respective positions the ultrasonic wavefront is steered; and
   determining one of the respective positions corresponds to a target position for measuring an accommodative effort of the eye associated with the ciliary processes based, at least in part, on the SNR of the reflected ultrasonic signals.

8. The at least one non-transitory machine-accessible storage medium of claim 5, providing additional instructions that, when executed by the machine, will cause the machine to perform further operations, comprising:
   activating individual ultrasonic transducers included in the plurality of ultrasonic transducers at different times in series and out of phase to form an ultrasonic wavefront directed towards the ciliary processes.

9. An ophthalmic device, comprising:
   two or more ultrasonic transducers adapted to direct ultrasonic signals towards a ciliary body in an eye;
   an accommodation actuator adapted to focus light entering the eye; and
   a controller coupled to the two or more ultrasonic transducers and the accommodation actuator, wherein the controller includes logic that when executed by the controller causes the ophthalmic device to perform operations including:
      emitting the ultrasonic signals from the two or more ultrasonic transducers towards the ciliary body;
      receiving reflected ultrasonic signals from the ciliary body, respectively, with the two or more ultrasonic transducers;
      determining a differential signal based on the reflected ultrasonic signals; and
      adjusting an optical power of the accommodation actuator based on the differential signal.

10. The ophthalmic device of claim 9, wherein the controller includes additional logic that when executed by the controller causes the ophthalmic device to perform further operations, including:
   determining a degree of displacement for the ciliary body based on the differential signal, wherein the degree of displacement is indicative of a level of accommodative effort of the eye, and wherein the optical power of the accommodation actuator is further based on the degree of displacement.

11. The ophthalmic device of claim 9, wherein the accommodation actuator includes a plurality of different levels of optical power, each associated with a respective level included in different levels of ciliary displacement.

12. The ophthalmic device of claim 11, wherein the controller includes additional logic that when executed by the controller causes the ophthalmic device to perform further operations, including:
   determining a degree of displacement for the ciliary body based on the differential signal; and
   rounding the degree of displacement to a nearest one of the different levels of ciliary displacement, and
   wherein the optical power of the accommodation actuator is adjusted to a corresponding one of the plurality of different levels of optical power associated with the nearest one of the different levels of ciliary displacement.

13. The ophthalmic device of claim 9, wherein the two or more ultrasonic transducers includes a first ultrasonic transducer and a second ultrasonic transducer, and wherein the first ultrasonic transducer is positioned within the ophthalmic device diametrically opposed to the second ultrasonic transducer.

14. The ophthalmic device of claim 9, wherein a width of the ultrasonic signals spans more than one ciliary process included in ciliary processes of the ciliary body, and wherein the ultrasonic signals are directed towards the ciliary processes included in the ciliary body.

15. The ophthalmic device of claim 9, wherein the ophthalmic device corresponds to a contact lens, an intraocular lens, or an intraocular implant.

16. The ophthalmic device of claim 9, wherein the two or more ultrasonic transducers includes a micromachined ultrasonic transducer (MUT), and wherein the MUT is included in a plurality of MUTs collectively arranged into an array to form one or more ultrasonic wavefronts.

17. At least one non-transitory machine-accessible storage medium that provides instructions that, when executed by a machine, will cause the machine to perform operations comprising:
   emitting ultrasonic signals from two or more ultrasonic transducers towards a ciliary body in an eye;
   receiving reflected ultrasonic signals from the ciliary body, respectively, with the two or more ultrasonic transducers;
   determining a differential signal based on the reflected ultrasonic signals; and
   adjusting an optical power of an accommodation actuator based on the differential signal.

18. The at least one non-transitory machine-accessible storage medium of claim 17, that provides additional instructions that, when executed by a machine, will cause the machine to perform further operations comprising:
   determining a degree of displacement for the ciliary body based on the differential signal, wherein the degree of displacement is indicative of a level of accommodative effort of the eye, and wherein the optical power of the accommodation actuator is further based on the degree of displacement.

19. The at least one non-transitory machine-accessible storage medium of claim 17, that provides additional instructions that, when executed by a machine, will cause the machine to perform further operations comprising:
  determining a degree of displacement for the ciliary body based on the differential signal, wherein the accommodation actuator includes a plurality of different levels of optical power, each associated with a respective level included in different levels of the ciliary displacement; and
  rounding the degree of displacement to a nearest one of the different levels of ciliary displacement, and
  wherein the optical power of the accommodation actuator is adjusted to a corresponding one of the plurality of different levels of optical power associated with the nearest one of the different levels of ciliary displacement.

20. The at least one non-transitory machine-accessible storage medium of claim 17, that provides additional instructions that, when executed by a machine, will cause the machine to perform further operations comprising:
  configuring the two or more ultrasonic transducers to emit the ultrasonic signals with a width spanning more than one ciliary process included in ciliary processes of the ciliary body, and wherein the ultrasonic signals are directed towards the ciliary processes included in the ciliary body.

\* \* \* \* \*